US008148077B2

(12) United States Patent
Abad et al.

(10) Patent No.: US 8,148,077 B2
(45) Date of Patent: Apr. 3, 2012

(54) METHOD FOR IDENTIFYING NOVEL GENES

(75) Inventors: Andre R. Abad, W. Des Moines, IA (US); Hua Dong, Johnston, IA (US); Susan B. Lo, West Des Moines, IA (US); Billy F. McCutchen, College Station, TX (US); Xiaomei Shi, Johnston, IA (US)

(73) Assignees: Pioneer Hi-Bred International, Inc., Johnston, IA (US); E.I. Dupont De Nemours and Company, Wilmington, DE (US)

( * ) Notice: Subject to any disclaimer, the term of this patent is extended or adjusted under 35 U.S.C. 154(b) by 680 days.

(21) Appl. No.: 11/780,884

(22) Filed: Jul. 20, 2007

(65) Prior Publication Data

US 2008/0026392 A1    Jan. 31, 2008

Related U.S. Application Data

(60) Provisional application No. 60/832,423, filed on Jul. 21, 2006.

(51) Int. Cl.
*C12P 19/34* (2006.01)
(52) U.S. Cl. .................................................... 435/6.12
(58) Field of Classification Search .................. None
See application file for complete search history.

(56) References Cited

U.S. PATENT DOCUMENTS

| | | | | |
|---|---|---|---|---|
| 5,204,237 | A | * | 4/1993 | Gaertner et al. ............. 435/6 |
| 5,506,099 | A | | 4/1996 | Carozzi et al. |
| 6,593,293 | B1 | | 7/2003 | Baum et al. |
| 2004/0072242 | A1 | * | 4/2004 | Hunter et al. .............. 435/7.1 |
| 2007/0243536 | A1 | * | 10/2007 | Abad et al. ................. 435/6 |

OTHER PUBLICATIONS

Arantes et al. Rev. Brasil. Genet. (Brazilian Journal of Genetics), 13, 4, p. 645 to p. 652, 1990.*
Kalman et al. Applied and Environmental Microbiology, Apr. 1993, p. 1131-1137.*
Duby et al. In Current Protocols in Molecular Biology (1993) 6.4.1-6.4.10.*
Morse et al. Structure, vol. 9, 409-417, 2001.*

Ben-Dov, Eitan et al., "Extended Screening by PCR for Seven *cry*-Group Genes from Field-Collected Strains of *Bacillus thuringiensis*," *Applied and Environmental Microbiology*, 1997, pp. 4883-4890, vol. 63, No. 12.
Carozzi, Nadine B., et al., "Prediction of Insecticidal Activity of *Bacillus thuringiensis* Strains by Polymerase Chain Reaction Product Profiles," *Applied and Environmental Microbiology*, 1991, pp. 3057-3061, vol. 57, No. 11.
Cerón, J., et al., "Specific PCR Primers Directed to Identify *cry*I and *cry*III Genes within a *Bacillus thuringiensis* Strain Collection," *Applied and Environmental Microbiology*, 1995, pp. 3826-3831, vol. 61, No. 11.
Juarez-Perez, V. M. et al., "PCR-Based Approach for Detection of Novel *Bacillus thuringiensis cry* Genes," *Applied and Environmental Microbiology*, 1997, pp. 2997-3002, vol. 63 No. 8.
Kalman, Sue et al., "Cloning of a Novel cryIC-Type Gene from a Strain of *Bacillus thuringensis* subsp. *galleriae*," *Applied and Environmental Microbiology*, 1993, pp. 1131-1137, vol. 59, No. 4.
Kaur, Sarvjeet, "Molecular Approaches for Identification and Construction of Novel Insecticidal Genes for Crop Protection," *World Journal of Microbiology & Biotechnology*, 2006, pp. 233-253, vol. 22.
Kuo, White-Shang et al., "Identification of Novel *cry*-Type Genes From *Bacillus thuringiensis* Strains on the Basis of Restriction Fragment Length Polymorphism of the PCR-Amplified DNA," 1996, pp. 1369-1377, vol. 62, No. 4.
Song, F. et al., "Identification of *cry*II-Type Genes from *Bacillus thuringiensis* Strains and Characterization of a Novel *cry*II-Type Gene," *Applied and Environmental Microbiology*, 2003, pp. 5207-5211, vol. 69, No. 9.

* cited by examiner

*Primary Examiner* — Samuel Woolwine
*Assistant Examiner* — Suchira Pande
(74) *Attorney, Agent, or Firm* — Alston & Bird LLP

(57) ABSTRACT

Methods and compositions for identifying novel genes that share regions of homology with known genes from target groups of genes of interest are provided. The methods comprise systematically designing oligonucleotide primers that are specific for regions of homology within the nucleotide sequences of a target group of known genes and performing successive rounds of PCR amplification of nucleic acid material from an organism of interest. The PCR steps are intended to identify and amplify nucleic acids comprising both known and novel genes. Nucleic acid molecules comprising known genes are detected and eliminated from further consideration by dot blot analysis using oligonucleotide probes specific for the known genes in the target group. Potentially novel genes are subjected to further sequence analysis to confirm novelty and assayed for biological activity. Compositions of the present invention include novel polynucleotides, and variants and fragments thereof, that comprise novel genes and the polypeptides encoded thereby.

36 Claims, 1 Drawing Sheet

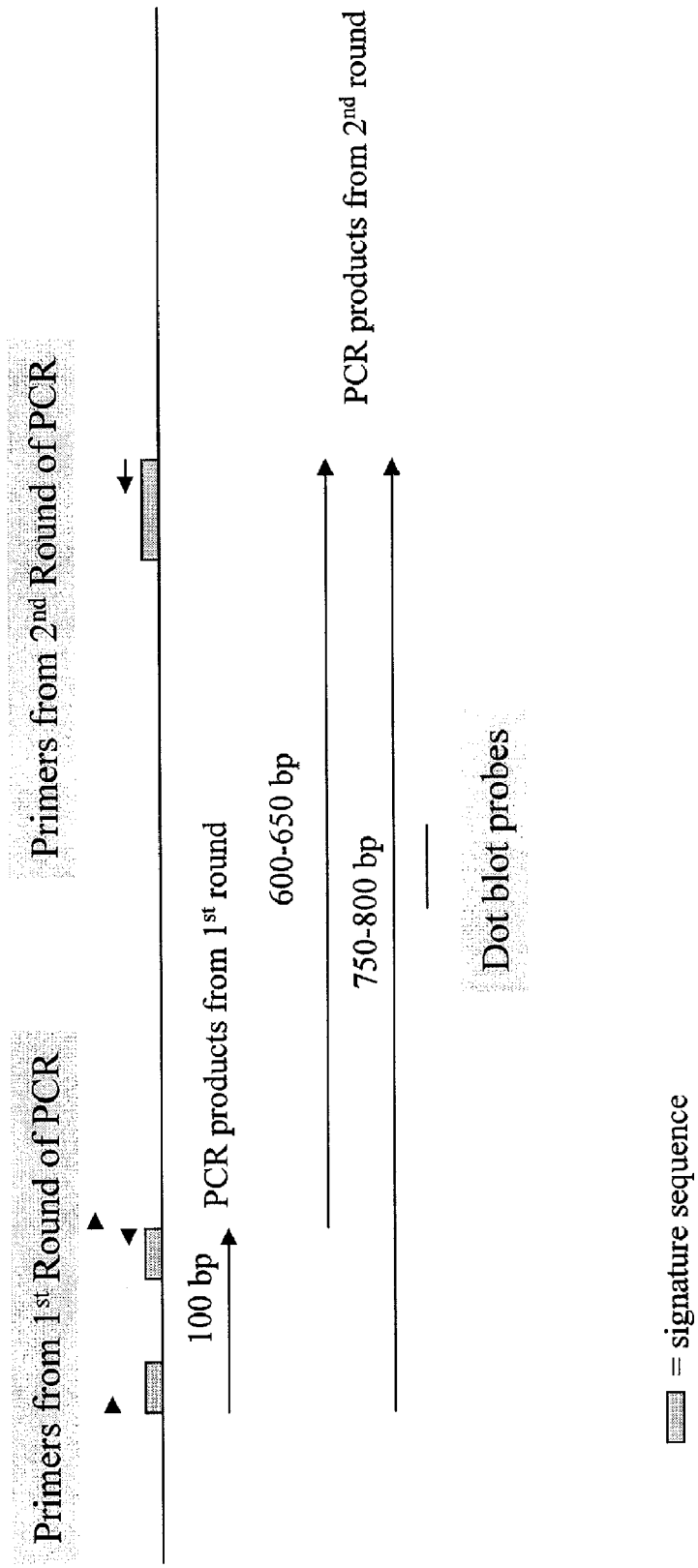

SEQUENCE LISTING

```
<160> NUMBER OF SEQ ID NOS: 6

<210> SEQ ID NO 1
<211> LENGTH: 2214
<212> TYPE: DNA
<213> ORGANISM: Bacillus thuringiensis

<400> SEQUENCE: 1 atg gag aat aat att caa aat caa tgc gtt cct tat aat tgt cta agc      48 acc cct gag aaa ata cta tta gat gag gaa aga att gag act ggg aat      96 aca tca atc gat ctt tct ttg tcg ctt gtg agc ctt ctt tta ggt gaa     144 ttc gtc cct ggt gcg tca ttt gta cta ggt cta att gat ata ata tgg     192 gga ttt gca ggt ccc tct caa tgg gac gca ttt ctg gta cag att gaa     240 cag tta att gac gaa aga ata ggt cag ttc gca agg aat caa gca att     288 tct aga tta gaa ggg cta agc aat ctc tat caa ata tac gca gaa gat     336 ttt aca cag tgg gaa gca gat ccc gat aat cca gca tta aga gaa gag     384 atg cgt act caa ttc aat gat atg aac agt gct ctt aca acc gct att     432 cct ctt ttg gca gtt caa aac tat caa att cct ctt tta tca gta tat     480 gtt caa gct gca aat tta cat tta tca gtt ttg aga gat gtt tca gtg     528 ttt gga caa agt tgg gga ttt gat gcg gcg act att aat agt cgt tat     576 aat gat tta act agg ctt att agc agc tat aca gat cat gta gta aga     624 tgg tat gat aca gga tta gac cgt ttg cga ggc tct act tac caa gac     672 tgg ttt aga tac aac cga ttt aga aga gaa tta aca ttg act gca tta     720 gat atc gtt gct ctt ttc cca aac tat gat atc aaa atg tat cca atc     768 caa ccc gtt agc caa cta aca agg gaa gtt tat acg gac cca tta att     816 aat ttc aat ccg cag tta cag tct gta gct caa ttg cct act ttt aac     864 gtt atg gaa agt aac gca att aga aac cct cat tta gtt gac ttc ttg     912
```

```
aat aac ctt aga att ttt aca gat tgg ttt agt gtc gga cgg cac tat      960
tat tgg gga gga cat cga gtg att tcc aaa cgt gta gga gga agg gag     1008
ata acc ttc cct ata tat gga agg gag gca aag cag gaa cct cca aga     1056
tcc ttt act ttt aat gga cct gtt ttt agg acg tta tca aat cct acc     1104
cta aga cca tta caa caa cct gca cca gct cct cct ttt aat tta cgt     1152
ggc ttg gaa ggt gta gaa ttt tat aca cct aca aat acc ttt acg tat     1200
cgg gga aga ggc ccg cgt gat tct tta act gaa tta ccg cct gga gat     1248
aca agt gta cta cct cgc gaa gga tat agt cac cgg tta tgt cat gca     1296
aca ttt att caa aga tct ggc aca cct ttt tta aca aca ggc gta gtc     1344
ttt tct tgg aca cat cgt agt gct gat gaa acg aat ata att tat cca     1392
gat aag att act caa att cca tgg gta aag gcg cat acc ctt gaa tcg     1440
ggg gcc act gtt att aag ggt cct gga ttt aca gga ggg gat att ctt     1488
act gtt ctt act agt ctt ggt tcc ttg ggc gct tta cga gta act ttt     1536
acg ggg caa tta cca caa aca tat aat ata cga atc cga tat gcc tcg     1584
gtg cta aat aaa tat ggt aca ctc cat ttt tca cag cca cct gca tat     1632
ggg ctc aca ttt cca aaa act atg gat ata gat gaa cca tta aca tct     1680
cgc tcg ttt gct ttt aca act ctt tgg aca cca ata acc ttt aca cga     1728
gca caa gag gaa ttt aat cta aca ata caa tca ggt gtt tat ata gat     1776
aga att gaa ttt gtt ccg gca gaa gta aca ttt gag gca gac tat gac     1824
ttg gaa aaa gcg caa aag gcg gtg aat gct ttg ttt act tct aaa aac     1872
caa agg ggg cta aaa aca gag gtg acg gat tat cat att gat caa gta     1920
tct aat tta gtc gaa tgt tta tcc gat gag ttt tgc cta gat gaa aag     1968
cga gaa tta cct gag aaa gtc aaa cag gcg aag cga ctc agt gat gag     2016
cga aac cta ctt caa gat tca aaa ttt agg gga atc aac agg caa cca     2064
gac agc gga tgg aga gga agt acg gat att acc atc caa gga gga gat     2112
gac gta ttc aaa gag aat tac gtc aca cta cca ggt acc ttt gat gag     2160
tgc tat cct aag cgg ccg caa gcc gaa ttc cag cac act ggc ggc cgt     2208
tac tag                                                              2214
```

<210> SEQ ID NO 2
<211> LENGTH: 737
<212> TYPE: PRT
<213> ORGANISM: Bacillus thuringiensis

<400> SEQUENCE: 2

```
Met Glu Asn Asn Ile Gln Asn Gln Cys Val Pro Tyr Asn Cys Leu Ser
  1               5                  10                  15

Thr Pro Glu Lys Ile Leu Leu Asp Glu Glu Arg Ile Glu Thr Gly Asn
             20                  25                  30

Thr Ser Ile Asp Leu Ser Leu Ser Leu Val Ser Leu Leu Gly Glu
         35                  40                  45

Phe Val Pro Gly Ala Ser Phe Val Leu Gly Leu Ile Asp Ile Ile Trp
     50                  55                  60

Gly Phe Ala Gly Pro Ser Gln Trp Asp Ala Phe Leu Val Gln Ile Glu
 65                  70                  75                  80
```

-continued

Gln Leu Ile Asp Glu Arg Ile Gly Gln Phe Ala Arg Asn Gln Ala Ile
            85                  90                  95

Ser Arg Leu Glu Gly Leu Ser Asn Leu Tyr Gln Ile Tyr Ala Glu Asp
            100                 105                 110

Phe Thr Gln Trp Glu Ala Asp Pro Asp Asn Pro Ala Leu Arg Glu Glu
            115                 120                 125

Met Arg Thr Gln Phe Asn Asp Met Asn Ser Ala Leu Thr Thr Ala Ile
            130                 135                 140

Pro Leu Leu Ala Val Gln Asn Tyr Gln Ile Pro Leu Leu Ser Val Tyr
145                 150                 155                 160

Val Gln Ala Ala Asn Leu His Leu Ser Val Leu Arg Asp Val Ser Val
                165                 170                 175

Phe Gly Gln Ser Trp Gly Phe Asp Ala Ala Thr Ile Asn Ser Arg Tyr
            180                 185                 190

Asn Asp Leu Thr Arg Leu Ile Ser Ser Tyr Thr Asp His Val Val Arg
            195                 200                 205

Trp Tyr Asp Thr Gly Leu Asp Arg Leu Arg Gly Ser Thr Tyr Gln Asp
            210                 215                 220

Trp Phe Arg Tyr Asn Arg Phe Arg Arg Glu Leu Thr Leu Thr Ala Leu
225                 230                 235                 240

Asp Ile Val Ala Leu Phe Pro Asn Tyr Asp Ile Lys Met Tyr Pro Ile
            245                 250                 255

Gln Pro Val Ser Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
            275                 280                 285

Val Met Glu Ser Asn Ala Ile Arg Asn Pro His Leu Val Asp Phe Leu
290                 295                 300

Asn Asn Leu Arg Ile Phe Thr Asp Trp Phe Ser Val Gly Arg His Tyr
305                 310                 315                 320

Tyr Trp Gly Gly His Arg Val Ile Ser Lys Arg Val Gly Gly Arg Glu
            325                 330                 335

Ile Thr Phe Pro Ile Tyr Gly Arg Glu Ala Lys Gln Glu Pro Pro Arg
            340                 345                 350

Ser Phe Thr Phe Asn Gly Pro Val Phe Arg Thr Leu Ser Asn Pro Thr
            355                 360                 365

Leu Arg Pro Leu Gln Gln Pro Ala Pro Pro Phe Asn Leu Arg
            370                 375                 380

Gly Leu Glu Gly Val Glu Phe Tyr Thr Pro Thr Asn Thr Phe Thr Tyr
385                 390                 395                 400

Arg Gly Arg Gly Pro Arg Asp Ser Leu Thr Glu Leu Pro Pro Gly Asp
            405                 410                 415

Thr Ser Val Leu Pro Arg Glu Gly Tyr Ser His Arg Leu Cys His Ala
            420                 425                 430

Thr Phe Ile Gln Arg Ser Gly Thr Pro Phe Leu Thr Thr Gly Val Val
            435                 440                 445

Phe Ser Trp Thr His Arg Ser Ala Asp Glu Thr Asn Ile Ile Tyr Pro
450                 455                 460

Asp Lys Ile Thr Gln Ile Pro Trp Val Lys Ala His Thr Leu Glu Ser
465                 470                 475                 480

Gly Ala Thr Val Ile Lys Gly Pro Gly Phe Thr Gly Gly Asp Ile Leu
            485                 490                 495

Thr Val Leu Thr Ser Leu Gly Ser Leu Gly Ala Leu Arg Val Thr Phe
            500                 505                 510

-continued

```
Thr Gly Gln Leu Pro Gln Thr Tyr Asn Ile Arg Ile Arg Tyr Ala Ser
        515                 520                 525

Val Leu Asn Lys Tyr Gly Thr Leu His Phe Ser Gln Pro Pro Ala Tyr
    530                 535                 540

Gly Leu Thr Phe Pro Lys Thr Met Asp Ile Asp Glu Pro Leu Thr Ser
545                 550                 555                 560

Arg Ser Phe Ala Phe Thr Thr Leu Trp Thr Pro Ile Thr Phe Thr Arg
                565                 570                 575

Ala Gln Glu Glu Phe Asn Leu Thr Ile Gln Ser Gly Val Tyr Ile Asp
            580                 585                 590

Arg Ile Glu Phe Val Pro Ala Glu Val Thr Phe Glu Ala Asp Tyr Asp
        595                 600                 605

Leu Glu Lys Ala Gln Lys Ala Val Asn Ala Leu Phe Thr Ser Lys Asn
    610                 615                 620

Gln Arg Gly Leu Lys Thr Glu Val Thr Asp Tyr His Ile Asp Gln Val
625                 630                 635                 640

Ser Asn Leu Val Glu Cys Leu Ser Asp Glu Phe Cys Leu Asp Glu Lys
                645                 650                 655

Arg Glu Leu Pro Glu Lys Val Lys Gln Ala Lys Arg Leu Ser Asp Glu
            660                 665                 670

Arg Asn Leu Leu Gln Asp Ser Lys Phe Arg Gly Ile Asn Arg Gln Pro
        675                 680                 685

Asp Ser Gly Trp Arg Gly Ser Thr Asp Ile Thr Ile Gln Gly Gly Asp
    690                 695                 700

Asp Val Phe Lys Glu Asn Tyr Val Thr Leu Pro Gly Thr Phe Asp Glu
705                 710                 715                 720

Cys Tyr Pro Lys Arg Pro Gln Ala Glu Phe Gln His Thr Gly Gly Arg
                725                 730                 735

Tyr

<210> SEQ ID NO 3
<211> LENGTH: 2013
<212> TYPE: DNA
<213> ORGANISM: Bacillus thuringiensis

<400> SEQUENCE: 3 atg aat tca tat aaa aat aaa aat gaa tat gaa ata ttg gat gct tca      48 cga aac aac tct act atg tct act cat tat cca agg tat cca cta gca      96 aat aat cca caa gct tct atg caa aat acg aat tat aaa gac tgg cta     144 aac atg tgt aca aat aat aac ctt att cct ata gaa cct gta gat ttc     192 acc tgg caa aat gtt ctt gtt tca acc ttc gct atc gct gca gct atc     240 gga aca ttg tta acc gct cca att act ggt gga aca tct ctg gta gct     288 gga tca gct ata ata gcc gct ata tta cca ctg acc ttc ccc gct aat     336 gat act agt gtt ccg gat aag ctt atg gat gcc ata caa gat tta gtt     384 agg cgt gag ata gat cag tac gtt aga aat aga gca aat tcg gag cta     432 ctc agc ttg aga gca cag ttg gat tct ttt aaa ggg cta ttt gat tat     480 tgg cgc gcc aac caa ggc aat cca aat gca act aat tca gtt agt cag     528 cgc ttt act gca gtt cat aat aat ttc ata ggg gca atg gca ctc ttt     576 aaa ata gag ggg tat gaa gaa tta ctg tta cca gta tat gtt cag gct     624 gca cgt tgg cat ttg ttc cat tta aga gat ggt atc acg tac gcc gat     672
```

-continued

```
caa tgg cag tta gct gat cca act cat gca act aat gca gga gag tac    720
cac tat agt gaa ttt aag aaa tat tct gcg caa tat gca gat cat tgt    768
gaa tta gta att aag aat cag cta gat aag att aaa aat gac tca aat    816
aaa aca tgg aaa gac tac aat caa tat cgt cga att atg aca ttt gct    864
gtt tcg gat att gtt gct gaa ttt tca atc att gat cca att tta tat    912
aaa gga ggg ata aat agg gaa att tta acg agg aaa ata tat aca gac    960
cct gtt aat ttt tca cct ggt gat tca att gca gat gat gaa aat aga   1008
tat aca gtc cca cca tca gct gtt aga aaa cta gtc ggc gca aca tta   1056
ttt act tct cag acg cct gct gat cct gat gtg gag ggt gag ttt att   1104
gga aat cga aac cgt tat tta cgt tta gaa ggt gga gaa cca ttt gat   1152
ggt cct caa atc gga aac tcg aca agc cgt tcg ata cca gta gga atc   1200
ccg aca act gaa tcg gtt tat gaa gtt ggt gta agg ggg cgt agt ggg   1248
gct cca cgt att tta ggt ttg aga tgg ggt tcg tta act gac ttt caa   1296
cag ttt agt gct gga gga gac gtg tat aat tta gtt atg aat agg gtt   1344
tct ttg cca cct gga gac aga ttc ccc ata aat gct ttt aat ttt act   1392
tat cga tta tca gat ata att ctt cct gga aat aag gga tca tct ttt   1440
gca tgg act cat cgt gag gtc gat cct aca gga aac tat tta tca aca   1488
aat cag att aat tta ata cct gct aca aaa ttt tct gaa aca cca tct   1536
tca cta ggg ata ctc aag gga ccg gga ttt ata ggg gga gat tta gtc   1584
gaa gtt tca tat acc gga att tct tat aag ttt aaa ttg aga tcc gtt   1632
agc tca act agt ttt aga att cgt gta cgt tat gca ggt tct ggt acg   1680
ggt cct tcg ctt agt ggg cag ata tat ttt aaa tta ggg aat gat atg   1728
tct cca gca act cct tgg ttg aat act gga ttt aac tct tcc aat gcg   1776
atg tat aat cac ttt aaa gta tta gag ctt tat gga act gca caa aat   1824
att aca gac aac aac ttg gag att ata gta agg tca gca agc tca ggt   1872
gct gag cgg ttt tat cta gaa aga ttg gaa ata atc cca att ggg ata   1920
cca aca gaa tac gct gaa tca caa aaa ttg gaa aca gca aag aaa gca   1968
gtg acc gac ttg ttt cca att aaa aca aag tat tta ctg aag tag      2013
```

<210> SEQ ID NO 4
<211> LENGTH: 670
<212> TYPE: PRT
<213> ORGANISM: Bacillus thuringiensis

<400> SEQUENCE: 4

```
Met Asn Ser Tyr Lys Asn Lys Asn Glu Tyr Glu Ile Leu Asp Ala Ser
 1               5                  10                  15

Arg Asn Asn Ser Thr Met Ser Thr His Tyr Pro Arg Tyr Pro Leu Ala
            20                  25                  30

Asn Asn Pro Gln Ala Ser Met Gln Asn Thr Asn Tyr Lys Asp Trp Leu
        35                  40                  45

Asn Met Cys Thr Asn Asn Leu Ile Pro Ile Glu Pro Val Asp Phe
    50                  55                  60

Thr Trp Gln Asn Val Leu Val Ser Thr Phe Ala Ile Ala Ala Ala Ile
65                  70                  75                  80
```

-continued

```
Gly Thr Leu Leu Thr Ala Pro Ile Thr Gly Thr Ser Leu Val Ala
                85                  90                  95

Gly Ser Ala Ile Ile Ala Ala Ile Leu Pro Leu Thr Phe Pro Ala Asn
            100                 105                 110

Asp Thr Ser Val Pro Asp Lys Leu Met Asp Ala Ile Gln Asp Leu Val
            115                 120                 125

Arg Arg Glu Ile Asp Gln Tyr Val Arg Asn Arg Ala Asn Ser Glu Leu
        130                 135                 140

Leu Ser Leu Arg Ala Gln Leu Asp Ser Phe Lys Gly Leu Phe Asp Tyr
145                 150                 155                 160

Trp Arg Ala Asn Gln Gly Asn Pro Asn Ala Thr Asn Ser Val Ser Gln
                165                 170                 175

Arg Phe Thr Ala Val His Asn Asn Phe Ile Gly Ala Met Ala Leu Phe
            180                 185                 190

Lys Ile Glu Gly Tyr Glu Glu Leu Leu Leu Pro Val Tyr Val Gln Ala
            195                 200                 205

Ala Arg Trp His Leu Phe His Leu Arg Asp Gly Ile Thr Tyr Ala Asp
        210                 215                 220

Gln Trp Gln Leu Ala Asp Pro Thr His Ala Thr Asn Ala Gly Glu Tyr
225                 230                 235                 240

His Tyr Ser Glu Phe Lys Lys Tyr Ser Ala Gln Tyr Ala Asp His Cys
                245                 250                 255

Glu Leu Val Ile Lys Asn Gln Leu Asp Lys Ile Lys Asn Asp Ser Asn
            260                 265                 270

Lys Thr Trp Lys Asp Tyr Asn Gln Tyr Arg Arg Ile Met Thr Phe Ala
        275                 280                 285

Val Ser Asp Ile Val Ala Glu Phe Ser Ile Ile Asp Pro Ile Leu Tyr
290                 295                 300

Lys Gly Gly Ile Asn Arg Glu Ile Leu Thr Arg Lys Ile Tyr Thr Asp
305                 310                 315                 320

Pro Val Asn Phe Ser Pro Gly Asp Ser Ile Ala Asp Asp Glu Asn Arg
                325                 330                 335

Tyr Thr Val Pro Pro Ser Ala Val Arg Lys Leu Val Gly Ala Thr Leu
            340                 345                 350

Phe Thr Ser Gln Thr Pro Ala Asp Pro Asp Val Glu Gly Glu Phe Ile
        355                 360                 365

Gly Asn Arg Asn Arg Tyr Leu Arg Leu Glu Gly Glu Pro Phe Asp
        370                 375                 380

Gly Pro Gln Ile Gly Asn Ser Thr Ser Arg Ser Ile Pro Val Gly Ile
385                 390                 395                 400

Pro Thr Thr Glu Ser Val Tyr Glu Val Gly Val Arg Gly Arg Ser Gly
                405                 410                 415

Ala Pro Arg Ile Leu Gly Leu Arg Trp Gly Ser Leu Thr Asp Phe Gln
            420                 425                 430

Gln Phe Ser Ala Gly Gly Asp Val Tyr Asn Leu Val Met Asn Arg Val
        435                 440                 445

Ser Leu Pro Pro Gly Asp Arg Phe Pro Ile Asn Ala Phe Asn Phe Thr
450                 455                 460

Tyr Arg Leu Ser Asp Ile Ile Leu Pro Gly Asn Lys Gly Ser Ser Phe
465                 470                 475                 480

Ala Trp Thr His Arg Glu Val Asp Pro Thr Gly Asn Tyr Leu Ser Thr
                485                 490                 495

Asn Gln Ile Asn Leu Ile Pro Ala Thr Lys Phe Ser Glu Thr Pro Ser
            500                 505                 510
```

-continued

Ser Leu Gly Ile Leu Lys Gly Pro Gly Phe Ile Gly Gly Asp Leu Val
    515                 520                 525

Glu Val Ser Tyr Thr Gly Ile Ser Tyr Lys Phe Lys Leu Arg Ser Val
530                 535                 540

Ser Ser Thr Ser Phe Arg Ile Arg Val Arg Tyr Ala Gly Ser Gly Thr
545                 550                 555                 560

Gly Pro Ser Leu Ser Gly Gln Ile Tyr Phe Lys Leu Gly Asn Asp Met
            565                 570                 575

Ser Pro Ala Thr Pro Trp Leu Asn Thr Gly Phe Asn Ser Ser Asn Ala
        580                 585                 590

Met Tyr Asn His Phe Lys Val Leu Glu Leu Tyr Gly Thr Ala Gln Asn
    595                 600                 605

Ile Thr Asp Asn Asn Leu Glu Ile Ile Val Arg Ser Ala Ser Ser Gly
    610                 615                 620

Ala Glu Arg Phe Tyr Leu Glu Arg Leu Glu Ile Ile Pro Ile Gly Ile
625                 630                 635                 640

Pro Thr Glu Tyr Ala Glu Ser Gln Lys Leu Glu Thr Ala Lys Lys Ala
            645                 650                 655

Val Thr Asp Leu Phe Pro Ile Lys Thr Lys Tyr Leu Leu Lys
        660                 665                 670

<210> SEQ ID NO 5
<211> LENGTH: 3491
<212> TYPE: DNA
<213> ORGANISM: Bacillus thuringiensis

<400> SEQUENCE: 5

```
atgaatagaa atgaatataa taaaaaagaa gtaaagccct cttcatcgaa tctttctccc      60
aaatacccac tgatgaattg tcttgatacg aaaagtcaaa atgttaatta taaagatagt     120
ttgaatgtta taaaggcga ttatcaagag ttagatccat caacgtcgac aagagcagct     180
tctgatgcga ttactgctgc ccttagtatt acctcaacaa tgttaggggc attaggtcac     240
ccaattactg gtgcgcttct aggcgttttt aatacactga caggattgtt gtggccaggc     300
ggggagatc ttacatggga agaattgttg gcggaaggtg aagaaatcat taataaaact     360
ataactgaaa gtataaaaaa tgatgctttg ctgcgattag aggaagcacg caaacaggta     420
gatgagtatt ctgggctttt aaatgattgg atattaaatc ctggtgtacg tattagtgct     480
gcaacaatga ggagtatttt tataactact gtacagcaat tagcagtaca gatggtatat     540
tttgaaaggg acaattatca aatccctctg ttaccagtat atgcacaagc tgcaaatcta     600
cacttagttg tattgaaaga tatcacaata ttcggggaag aatggggatt ccctgaaaca     660
gacattaatt tttattataa atcagaattt ttagaacata tagaggaata cactgattat     720
gttgtcaaat ggtataaaga agggttaaat gaattacaga agtcatcgtc tacagattgg     780
gttgcatata atcgttatcg aagagaaatg actatattgg cactggatat tattgcactc     840
ttcccggcat atgatggatt tttatatcca ttggagacaa acactgagtt gacaagagaa     900
gtgtatatgg accctgaagg tggcggacca actaactggc gtcaataccc aatctctttc     960
acgcaaatag aaaatttaat tcgtccgcct catttattta cttggctaaa ttccatacaa    1020
attgaaactg acaaggaatt aactgcgac gattattatg tatgtatgtg ggcaggtagt    1080
ttgctaggct tgcattatac aaattcgtca agtgttttca cagtgaaaaa tggcagtggt    1140
gactataaaa agctttatga tctctcaggg aaagatgttt atcaaacgtt attatacgca    1200
ggttcgagtc atgaagctgg ctttagcaaa gtcactgatt ttgttggaaa cgaaggtggg    1260
```

```
acttttaact tagtatctga gagtggtacc acaagctctt tttcttctgc actttgcgga    1320
atatcaaaca cacatcttat agattcagta acggtattac ctccggatat atcggaccca    1380
tctcaaagtc tttcaaagga ttatactcat agactatctt atgttactaa cgtgtcctat    1440
tatagaaatc agtctgttga ttttgatcga gtagagctac ccatattagg ttggacccat    1500
agaagtgtag gttttgataa tcgaatttat ccatataaaa ttacgcaggt tccagctgtg    1560
aaagctaata aactggataa tagtgctatg acagttgtag aagggccaaa ttttacaggt    1620
ggagccctag ttaaggtaaa cagcactggt ggtggtagat atagtttgaa attttctgtt    1680
aaggcagatc caaataactt atcgcaaaaa tattatataa gattacgata tgcaggtgaa    1740
tggcgtttca atcaaagtaa ttatagaagt tttactatta gtattaacgg caataaaatt    1800
gagggtaaag gattttttaag taatactaga ttggaaaccg atgaagttcc tacgcttttt    1860
aatgactttg ggtggaccag tattaaatct acctttactt ttccaaaatc ggaatgtgaa    1920
ataagtttgg atttttatga tgagaattca actattggac cagttgggcc agtattcatt    1980
gatagaattg aggttgtccc agcggatgat aattacggag aaaagaaaa tttagaaaaa    2040
gcacagaaag ccgtgaatgc cttgtttaca gcgggaagca tgcactcca acaggtgtg     2100
acagattaca aagtggacca ggtttcaatt ttagtggatt gtgtatcagg agagttatat    2160
cccaatgaga acgcgaact acaaaatcta atcaaatacg caaaacgttt gagctattcc    2220
cgtaatttac ttctagatcc aacattcgat tctatcaatt catctgagga gaatggctgg    2280
tacggcagta atggtattgc aattggaaat gggaatcttg tatttaaagg gaactatata    2340
attttctcag gtaccaatga tacacaatac ccaacgtatc tctatcaaaa aattgatgaa    2400
tccaagctta agaatatac acgctataaa ctgagaggt ttatcgagaa tagtcaagat    2460
ttagaagcat atgtggttcg ctatgatgca aaacatgaaa cattggatgt atccaataat    2520
ctattcccag atatttctcc tgtaaatgca tgcggagaac ccaatcgttg tgcggcacta    2580
ccatacctgg atgaaaatcc gaggttagaa tgtagttcga tacaagatgg catttatct    2640
gattcgcatt cattttctct caatatagat acaggttcta ttgattccaa tgagaacgta    2700
ggcatttggg tgttgtttaa aattccaca ccggaagggt atgcgaaatt tggaaaccta    2760
gaagtgattg aagatggccc ggtcattgga gaagcattag cccgtgtgaa acgtcaagaa    2820
acgaagtgga gaaacaagtt gacacaactg cgaacggaaa cacaagcgat ttatacacgc    2880
gcaaaacaag ccattgataa tttattcaca aatgcacagg actctcactt aaaaataggt    2940
gctacattcg cgtcaattgt ggctgcacga aagattgtcc aatccatacg tgaagcgtat    3000
atgtcatggt tatctatcgt cccaggtgta aattatccta ttttacaga gttgaatgag    3060
agagtacagc gagcatttca attatatgat gtacggaatg tcgtgcgtaa tggccgattc    3120
ctgaatggag tatcggattg gattgtgaca tctaatgtaa aggtacaaga agaaaatggg    3180
aacaatgtat tagttctttc caattgggat gcgcaagtat tacaatgtct gaagctctat    3240
caagatcgcg gatatatctt gcgtgtaacg gcacgtaaag aaggattggg agaaggatat    3300
attacaatta cggatgaaga agggcataca gatcaattga catttggcac atgtgaggaa    3360
atagatgcat ctaacacgtt cgtatccaca ggttatatta caaaagaact agaattttc    3420
ccagatacag agaaagtgcg tatagaaatt ggggagacag aaggaaccct ccaggtagaa    3480
agtgtagaat t                                                        3491

<210> SEQ ID NO 6
<211> LENGTH: 1163
```

<212> TYPE: PRT
<213> ORGANISM: Bacillus thuringiensis

<400> SEQUENCE: 6

```
Met Asn Arg Asn Glu Tyr Asn Lys Lys Glu Val Lys Pro Ser Ser Ser
 1               5                  10                  15

Asn Leu Ser Pro Lys Tyr Pro Leu Met Asn Cys Leu Asp Thr Lys Ser
             20                  25                  30

Gln Asn Val Asn Tyr Lys Asp Ser Leu Asn Val Ile Lys Gly Asp Tyr
         35                  40                  45

Gln Glu Leu Asp Pro Ser Thr Ser Thr Arg Ala Ala Ser Asp Ala Ile
     50                  55                  60

Thr Ala Leu Ser Ile Thr Ser Thr Met Leu Gly Ala Leu Gly His
 65                  70                  75                  80

Pro Ile Thr Gly Ala Leu Leu Gly Val Phe Asn Thr Leu Thr Gly Leu
                 85                  90                  95

Leu Trp Pro Gly Gly Asp Leu Thr Trp Glu Glu Leu Leu Ala Glu
             100                 105                 110

Gly Glu Glu Ile Ile Asn Lys Thr Ile Thr Glu Ser Ile Lys Asn Asp
         115                 120                 125

Ala Leu Leu Arg Leu Glu Glu Ala Arg Lys Gln Val Asp Glu Tyr Ser
    130                 135                 140

Gly Ala Leu Asn Asp Trp Ile Leu Asn Pro Gly Val Arg Ile Ser Ala
145                 150                 155                 160

Ala Thr Met Arg Ser Ile Phe Ile Thr Thr Val Gln Gln Leu Ala Val
                165                 170                 175

Gln Met Val Tyr Phe Glu Arg Asp Asn Tyr Gln Ile Pro Leu Leu Pro
            180                 185                 190

Val Tyr Ala Gln Ala Ala Asn Leu His Leu Val Val Leu Lys Asp Ile
        195                 200                 205

Thr Ile Phe Gly Glu Glu Trp Gly Phe Pro Glu Thr Asp Ile Asn Phe
    210                 215                 220

Tyr Tyr Lys Ser Glu Phe Leu Glu His Ile Glu Glu Tyr Thr Asp Tyr
225                 230                 235                 240

Val Val Lys Trp Tyr Lys Glu Gly Leu Asn Glu Leu Gln Lys Ser Ser
                245                 250                 255

Ser Thr Asp Trp Val Ala Tyr Asn Arg Tyr Arg Arg Glu Met Thr Ile
            260                 265                 270

Leu Ala Leu Asp Ile Ile Ala Leu Phe Pro Ala Tyr Asp Gly Phe Leu
        275                 280                 285

Tyr Pro Leu Glu Thr Asn Thr Glu Leu Thr Arg Glu Val Tyr Met Asp
    290                 295                 300

Pro Glu Gly Gly Gly Pro Thr Asn Trp Arg Gln Tyr Pro Ile Ser Phe
305                 310                 315                 320

Thr Gln Ile Glu Asn Leu Ile Arg Pro Pro His Leu Phe Thr Trp Leu
                325                 330                 335

Asn Ser Ile Gln Ile Glu Thr Asp Lys Glu Leu Thr Ala Asp Asp Tyr
            340                 345                 350

Tyr Val Cys Met Trp Ala Gly Ser Leu Leu Gly Leu His Tyr Thr Asn
        355                 360                 365

Ser Ser Ser Val Phe Thr Val Lys Asn Gly Ser Gly Asp Tyr Lys Lys
    370                 375                 380

Leu Tyr Asp Leu Ser Gly Lys Asp Val Tyr Gln Thr Leu Leu Tyr Ala
385                 390                 395                 400
```

```
Gly Ser Ser His Glu Ala Gly Phe Ser Lys Val Thr Asp Phe Val Gly
            405                 410                 415

Asn Glu Gly Gly Thr Phe Asn Leu Val Ser Glu Ser Gly Thr Thr Ser
        420                 425                 430

Ser Phe Ser Ser Ala Leu Cys Gly Ile Ser Asn Thr His Leu Ile Asp
            435                 440                 445

Ser Val Thr Val Leu Pro Pro Asp Ile Ser Asp Pro Ser Gln Ser Leu
        450                 455                 460

Ser Lys Asp Tyr Thr His Arg Leu Ser Tyr Val Thr Asn Val Ser Tyr
465                 470                 475                 480

Tyr Arg Asn Gln Ser Val Asp Phe Asp Arg Val Glu Leu Pro Ile Leu
                485                 490                 495

Gly Trp Thr His Arg Ser Val Gly Phe Asp Asn Arg Ile Tyr Pro Tyr
            500                 505                 510

Lys Ile Thr Gln Val Pro Ala Val Lys Ala Asn Lys Leu Asp Asn Ser
        515                 520                 525

Ala Met Thr Val Val Glu Gly Pro Asn Phe Thr Gly Gly Ala Leu Val
    530                 535                 540

Lys Val Asn Ser Thr Gly Gly Arg Tyr Ser Leu Lys Phe Ser Val
545                 550                 555                 560

Lys Ala Asp Pro Asn Asn Leu Ser Gln Lys Tyr Tyr Ile Arg Leu Arg
                565                 570                 575

Tyr Ala Gly Glu Trp Arg Phe Asn Gln Ser Asn Tyr Arg Ser Phe Thr
            580                 585                 590

Ile Ser Ile Asn Gly Asn Lys Ile Glu Gly Lys Gly Phe Leu Ser Asn
        595                 600                 605

Thr Arg Leu Glu Thr Asp Glu Val Pro Thr Leu Phe Asn Asp Phe Gly
    610                 615                 620

Trp Thr Ser Ile Lys Ser Thr Phe Thr Phe Pro Lys Ser Glu Cys Glu
625                 630                 635                 640

Ile Ser Leu Asp Phe Tyr Asp Glu Asn Ser Thr Ile Gly Pro Val Gly
                645                 650                 655

Pro Val Phe Ile Asp Arg Ile Glu Val Val Pro Ala Asp Asn Tyr
            660                 665                 670

Gly Glu Lys Glu Asn Leu Glu Lys Ala Gln Lys Ala Val Asn Ala Leu
        675                 680                 685

Phe Thr Ala Gly Arg His Ala Leu Gln Thr Gly Val Thr Asp Tyr Lys
    690                 695                 700

Val Asp Gln Val Ser Ile Leu Val Asp Cys Val Ser Gly Glu Leu Tyr
705                 710                 715                 720

Pro Asn Glu Lys Arg Glu Leu Gln Asn Leu Ile Lys Tyr Ala Lys Arg
                725                 730                 735

Leu Ser Tyr Ser Arg Asn Leu Leu Asp Pro Thr Phe Asp Ser Ile
            740                 745                 750

Asn Ser Ser Glu Glu Asn Gly Trp Tyr Gly Ser Asn Gly Ile Ala Ile
        755                 760                 765

Gly Asn Gly Asn Leu Val Phe Lys Gly Asn Tyr Ile Ile Phe Ser Gly
    770                 775                 780

Thr Asn Asp Thr Gln Tyr Pro Thr Tyr Leu Tyr Gln Lys Ile Asp Glu
785                 790                 795                 800

Ser Lys Leu Lys Glu Tyr Thr Arg Tyr Lys Leu Arg Gly Phe Ile Glu
                805                 810                 815

Asn Ser Gln Asp Leu Glu Ala Tyr Val Val Arg Tyr Asp Ala Lys His
            820                 825                 830
```

```
Glu Thr Leu Asp Val Ser Asn Asn Leu Phe Pro Asp Ile Ser Pro Val
        835                 840                 845

Asn Ala Cys Gly Glu Pro Asn Arg Cys Ala Ala Leu Pro Tyr Leu Asp
        850                 855                 860

Glu Asn Pro Arg Leu Glu Cys Ser Ser Ile Gln Asp Gly Ile Leu Ser
865             870                 875                 880

Asp Ser His Ser Phe Ser Leu Asn Ile Asp Thr Gly Ser Ile Asp Ser
            885                 890                 895

Asn Glu Asn Val Gly Ile Trp Val Leu Phe Lys Ile Ser Thr Pro Glu
            900                 905                 910

Gly Tyr Ala Lys Phe Gly Asn Leu Glu Val Ile Glu Asp Gly Pro Val
        915                 920                 925

Ile Gly Glu Ala Leu Ala Arg Val Lys Arg Gln Glu Thr Lys Trp Arg
    930                 935                 940

Asn Lys Leu Thr Gln Leu Arg Thr Glu Thr Gln Ala Ile Tyr Thr Arg
945             950                 955                 960

Ala Lys Gln Ala Ile Asp Asn Leu Phe Thr Asn Ala Gln Asp Ser His
            965                 970                 975

Leu Lys Ile Gly Ala Thr Phe Ala Ser Ile Val Ala Ala Arg Lys Ile
            980                 985                 990

Val Gln Ser Ile Arg Glu Ala Tyr Met Ser Trp Leu Ser Ile Val Pro
        995                 1000                1005

Gly Val Asn Tyr Pro Ile Phe Thr Glu Leu Asn Glu Arg Val Gln Arg
    1010                1015                1020

Ala Phe Gln Leu Tyr Asp Val Arg Asn Val Val Arg Asn Gly Arg Phe
1025            1030                1035                1040

Leu Asn Gly Val Ser Asp Trp Ile Val Thr Ser Asn Val Lys Val Gln
            1045                1050                1055

Glu Glu Asn Gly Asn Asn Val Leu Val Leu Ser Asn Trp Asp Ala Gln
            1060                1065                1070

Val Leu Gln Cys Leu Lys Leu Tyr Gln Asp Arg Gly Tyr Ile Leu Arg
            1075                1080                1085

Val Thr Ala Arg Lys Glu Gly Leu Gly Glu Gly Tyr Ile Thr Ile Thr
        1090                1095                1100

Asp Glu Glu Gly His Thr Asp Gln Leu Thr Phe Gly Thr Cys Glu Glu
1105            1110                1115                1120

Ile Asp Ala Ser Asn Thr Phe Val Ser Thr Gly Tyr Ile Thr Lys Glu
            1125                1130                1135

Leu Glu Phe Phe Pro Asp Thr Glu Lys Val Arg Ile Glu Ile Gly Glu
            1140                1145                1150

Thr Glu Gly Thr Phe Gln Val Glu Ser Val Glu
        1155                1160
```

METHOD FOR IDENTIFYING NOVEL GENES

CROSS REFERENCE TO RELATED APPLICATIONS

This application claims the benefit of U.S. Provisional Application No. 60/832,423, filed on Jul. 21, 2006, which is herein incorporated by reference in its entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 331411 SequenceListing.txt, a creation date of Jul. 18, 2007, and a size of 31.7 KB. The sequence listing filed via EFS-Web is part of the specification and is hereby incorporated in its entirety by reference herein.

FIELD OF THE INVENTION

The present invention relates to methods and compositions for identifying novel genes that are homologous to known genes, particularly *Bacillus thuringiensis* (Bt) Cry genes.

BACKGROUND OF THE INVENTION

Insect pests are a major factor in the loss of the world's agricultural crops. For example, corn rootworm feeding damage and boll weevil damage can be economically devastating to agricultural producers. Insect pest-related crop loss from corn rootworm alone has reached one billion dollars a year.

Traditionally, the primary methods for impacting insect pest populations, such as corn rootworm populations, are crop rotation and the application of broad-spectrum synthetic chemical pesticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternatives to traditional chemical pesticides that present a lower risk of pollution and environmental hazards and provide a greater target specificity than is characteristic of traditional broad-spectrum chemical insecticides.

Certain species of microorganisms of the genus *Bacillus* are known to possess pesticidal activity against a broad range of insect pests including Lepidoptera, Diptera, Coleoptera, Hemiptera, and others. *Bacillus thuringiensis* (Bt) and *Bacillus papilliae* are among the most successful biocontrol agents discovered to date. Insect pathogenicity has been attributed to strains of: *B. larvae, B. lentimorbus, B. papilliae, B. sphaericus*, Bt (Harwook, ed. (1989) *Bacillus* (Plenum Press), p. 306) and *B. cereus* (International Publication No. WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial pesticides, particularly those obtained from *Bacillus* strains, have played an important role in agriculture as alternatives to chemical pest control. Pesticidal proteins isolated from strains of Bt, known as δ-endotoxins or Cry toxins, are initially produced in an inactive protoxin form. These protoxins are proteolytically converted into an active toxin through the action of proteases in the insect gut. See, Rukmini et al. (2000) *Biochimie* 82:109-116; Oppert (1999) *Arch. Insect Biochem. Phys.* 42:1-12; and Carroll et al. (1997) *J. Invertebrate Pathology* 70:41-49. Proteolytic activation of the toxin can include the removal of the N- and C-terminal peptides from the protein, as well as internal cleavage of the protein. Once activated, the Cry toxin binds with high affinity to receptors on epithelial cells in the insect gut, thereby creating leakage channels in the cell membrane, lysis of the insect gut, and subsequent insect death through starvation and septicemia. See, e.g., Li et al. (1991) *Nature* 353:815-821.

Recently, agricultural scientists have developed crop plants with enhanced insect resistance by genetically engineering crop plants with pesticidal genes to produce pesticidal proteins from *Bacillus*. For example, corn and cotton plants genetically engineered to produce Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in American agriculture and have provided the farmer with an environmentally friendly alternative to traditional insect-control methods. In addition, potatoes genetically engineered to contain pesticidal Cry toxins have been developed. These successes with genetic engineering have led researchers to search for novel pesticidal genes, particularly Cry genes. Therefore, new methods for efficiently identifying novel pesticidal genes, including those that are homologous to known Cry genes as well as those that represent novel families of Cry genes, are needed in the art.

SUMMARY OF THE INVENTION

The present invention is directed to methods and compositions for identifying novel genes. The methods disclosed herein permit the rapid and efficient screening of a large number of nucleotide sequences to identify potential novel genes from a variety of organisms. The present methods for identifying novel genes permit the identification of genes that are homologous to known genes as well as completely novel genes that may be members of presently unidentified families of genes of interest, including pesticidal genes. In certain aspects of the invention, the methods permit the identification of novel pesticidal genes that are homologous to known pesticidal genes, including, for example, Bt Cry toxin genes.

The methods of the invention comprise systematically designing oligonucleotide primers that are specific for regions of homology (i.e., signature sequences) within a target group of known genes of interest (e.g., pesticidal genes) and performing a first round of PCR amplification of nucleic acid material from an organism of interest. The first round of PCR is intended to amplify both known and novel genes that contain the signature sequence. If PCR products are detected in the first round of PCR, a second sample of nucleic acid material from the organism is obtained and subjected to a second round of PCR using a second set of oligonucleotide primers that are specific for signature sequences within the target group of genes. PCR products from the second round of PCR are separated by agarose gel electrophoresis, and the resulting isolated nucleic acids cloned into cloning vectors, particularly bacterial cloning vectors. The cloning vectors are then transformed into competent host cells such as bacterial cells. Nucleic acid material isolated from individual host cell colonies is analyzed by dot blot hybridization analysis using labeled oligonucleotide probes that are specific for all known genes in the target group. The dot blot analysis step of the method of the invention is intended to identify and eliminate known genes from the target group from further consideration. PCR products amplified in the second round of PCR that are not detected by dot blot analysis comprise putative novel genes (e.g., novel pesticidal genes), or fragments thereof. These nucleic acids are subjected to further sequence analysis to confirm novelty and to determine nucleotide sequences. Putative novel genes are expressed and the recombinant proteins assayed to assess biological activity, such as pesticidal activity when the methods of the invention are used to identify novel pesticidal genes. The methods of the invention are further amenable to automation and high-throughput screening.

Compositions of the invention include novel isolated polynucleotides, and variants and fragments thereof, comprising novel genes, including, for example, novel pesticidal genes. Polypeptides encoded by the polynucleotides of the invention are also provided. Novel pesticidal genes (e.g., Bt Cry toxin genes) identified by the methods disclosed herein find use in protecting plants from pests, particularly insect pests, and pest-related damage.

BRIEF DESCRIPTION OF THE DRAWINGS

FIG. 1 provides a schematic representation of the design of oligonucleotide primers for use in the first and second rounds of PCR and oligonucleotide probes for dot blot analysis, as described in detail herein below.

DETAILED DESCRIPTION OF THE INVENTION

The present invention is directed to methods and compositions for identifying novel genes, particularly novel pesticidal genes, more particularly novel Bt Cry toxin genes. The methods of the invention permit the rapid and efficient screening of a large number of nucleotide sequences to identify putative novel genes that are homologous to known genes. As used herein, the term "target group of genes" refers to any collection of known genes from any organism of interest that comprises regions of homology. A "target group" in some embodiments may comprise a collection of known pesticidal genes, more particularly a group of known Bt Cry toxin genes. In general, the methods of the invention comprise three distinct steps for identifying novel genes from a target group: a first round of PCR, more particularly real-time PCR, a second round of PCR, and a dot blot analysis step. In particular embodiments, a first round of PCR amplification of nucleic acid material from an organism of interest is performed and is intended to amplify both known and novel genes comprising a targeted signature sequence. A "signature sequence" is intended to mean a region of homology that is present within all members of the target group of genes of interest. If PCR products are detected in the first round of PCR, a second round of PCR of a second sample of nucleic acid material from the organism is obtained and subjected to an additional round of PCR amplification. The second round of PCR is intended to amplify both known and novel genes that contain particular targeted signature sequences. PCR products from the second round are generally isolated for further analysis. The third step comprises performing dot blot analysis of the individual PCR products isolated in the second round of PCR. The dot blot analysis step is performed with oligonucleotide probes that are specific for known genes in the target group and, therefore, is intended to detect and eliminate known genes from further consideration. PCR products from the second round of PCR that are not detected by dot blot analysis comprise putative novel genes (e.g., novel pesticidal genes), or fragments thereof, and are subjected to further sequence analysis to confirm novelty. The sequences of putative novel genes are determined, and these nucleic acid molecules and the proteins encoded thereby are used in bioassays to assess biological activity, such as, for example, pesticidal activity.

More particularly, the methods for identifying novel genes comprise systematically designing oligonucleotide primers to regions of homology (i.e., signature sequences) within the target group of known genes, such as a target group of Bt pesticidal genes, and using these primers in a first round of PCR amplification of nucleic acid material from an organism of interest. In some aspects of the invention, the organism of interest is a microorganism, more particularly a Bt strain. The primers designed for the first round of PCR amplification are intended to amplify both known and novel genes containing the targeted signature sequences, as described in more detail below. If PCR products are detected in the first round of PCR, a second sample of nucleic acid material from the organism is obtained and subjected to a second round of PCR amplification.

The oligonucleotide primers used in the second round of PCR are also designed to amplify both known and novel genes (e.g., pesticidal genes) containing targeted signature sequences. The oligonucleotide primers used in the second round of PCR are generally designed to generate PCR products of a particular length (e.g., about 500 base pairs (bp) to about 800 bp in length, particularly about 600 bp to about 750 bp, more particularly about 650 bp to about 700 bp). PCR products of the expected length that are generated during the second round of PCR are isolated by, for example, agarose gel electrophoresis. Therefore, the second round of PCR permits the amplification of known and novel genes, or fragments thereof, containing particular signature sequences and permits the isolation of these nucleic acid molecules for further analysis.

PCR products from the second round of amplification that are of the expected length generally comprise fragments of known or novel genes. These nucleic acid fragments are cloned into cloning vectors (e.g., bacterial cloning vectors). The cloning vector inserts (i.e., the PCR products from the second round of PCR) comprise known and potentially novel genes from the target group, or likely fragments thereof, and are used to transform competent host cells, particularly bacterial cells such as, for example, *E. coli* cells. In particular aspects of the invention, nucleic acid material (e.g., plasmid DNA) is isolated from individual host cell (e.g., bacterial) colonies and analyzed by dot blot analysis using labeled oligonucleotide probes specific for all known genes within the target group. In particular embodiments, the oligonucleotide probes are designed to be complementary to fragments of the PCR products generated during the second round of amplification, as described herein below. Dot blot analysis with oligonucleotide probes that are specific for all known genes within the target group permits the identification of nucleic acid molecules comprising known genes (e.g., known Bt Cry toxin genes of a particular target group). Nucleic acids containing known genes are eliminated from further consideration. Nucleic acids that are not detected by dot blot analysis comprise putative novel genes, or fragments thereof, and are subjected to further sequence analysis and biological activity assays. In particular embodiments of the invention, the methods are used to identify novel pesticidal genes, particularly novel Bt Cry toxin genes, and, accordingly, putative novel pesticidal genes are further analyzed for pesticidal activity.

In certain aspects of the invention, PCR products generated in the second round of PCR that are not detected by dot blot analysis, as described above, are sequenced and compared with known sequences from public databases to assess novelty. If the sequence comparisons indicate that the PCR product contains a potentially novel gene, such as a novel pesticidal gene (e.g, a novel Bt Cry toxin gene), the full-length sequence is obtained using, for example, the GenomeWalker Universal Kit (Becton Dickinson Bioscience, Inc.). The resulting sequence is also compared against sequences in public databases to further verify novelty. In particular embodiments, novel genes are cloned into expression vectors and the proteins encoded thereby assayed for biological activity, such as pesticidal activity in the case of novel putative novel pesticidal genes.

The methods of the invention are directed to identifying novel genes, particularly pesticidal genes, more particularly Bt Cry toxin pesticidal genes. Although the methods of the invention are described herein below for the identification of pesticidal genes, such methods may be used to identify novel genes that are homologous to any group of known genes (i.e., a target group of interest) from any organism of interest. The description of the identification of novel pesticidal genes is intended to be merely exemplary and is not limiting.

The methods of the invention may be used to identify novel genes that are homologous to known Cry genes while also identifying genes that share little homology with previously identified Cry genes and that may actually represent novel families of Bt pesticidal genes. In one embodiment of the invention, nucleic acid material isolated from Bt strains of interest is subjected to a first round of PCR, generally real-time PCR, using at least one set of degenerate oligonucleotide primers that are specific for a region of homology (i.e., a signature sequence) present in all members of a target group of pesticidal genes. As used herein, "target group of pesticidal genes" refers to any collection of known pesticidal genes that comprise regions of homology. Members of the target group of pesticidal genes are aligned to design oligonucleotide primers. As indicated above, a region of homology that is present within all members of the target group of pesticidal genes is referred to as a "signature sequence." The signature sequences within the nucleotide sequences of the target group of pesticidal genes serve as the basis for designing oligonucleotide primers for use in the first and second rounds of PCR, as described in more detail below. In certain aspects of the invention, the target group comprises all known pesticidal Cry genes that are active against insects from the order Coleoptera (i.e., Coleopteran-active Cry genes). In other embodiments, the target group comprises, for example, all known Bt genes that have pesticidal activity against insects from the orders Lepidoptera and Coleoptera, excluding those Cry genes that are active against insects from the order Diptera. The target group of pesticidal genes is selected and defined by the researcher at the outset of the search for novel pesticidal genes.

Oligonucleotide primers specific for the target group of pesticidal genes are mixed with a first sample of nucleic acid material from a microorganism of interest and a DNA polymerase under conditions that are suitable for amplification by PCR. The methods of the present invention further comprise performing a first round of PCR and detecting the presence or absence of PCR amplification products. In particular embodiments, the first round of PCR comprises performing quantitative real-time PCR using a SYBR® Green dye to detect the presence of PCR products.

If PCR products are detected in the first round of PCR, a second sample of nucleic acid from the microorganism of interest is obtained and subjected to a second round of PCR. The oligonucleotide primers used in the second round of PCR are also specific for signature sequences within the nucleotide sequences of the target group of pesticidal genes, as described above. In general, the reverse oligonucleotide primers used in the first round of PCR are used to generate the forward primers for the second round of PCR, thereby serving as a bridge between the first and second rounds of PCR. The reverse primers used in the second round of PCR are designed to target a different signature sequence that is typically located 3' to the signature sequence used to design the reverse primers for the first round of PCR. The oligonucleotide primers for the second round of PCR are further designed to produce PCR products of a particular length, specifically about 500 bp to about 800 bp, particularly about 600 bp to about 750 bp, more particularly about 650 bp to about 700 bp. The PCR reactions from the second round of PCR amplification may be separated by agarose gel electrophoresis, and the resulting PCR products comprising nucleic acid fragments of the expected length are ligated into cloning vectors, particularly bacterial cloning vectors. The vectors are then transformed into competent host cells, for example, bacterial cells such as *E. coli* cells.

Examples of suitable host cells include, but are not limited to, bacterial cells, fungal cells, plant cells (dicotyledonous and monocotyledonous), and animal cells. In particular embodiments, the host cells are bacterial cells. Cloning vectors for delivery of polynucleotides to a variety of host cells are well known in the art. Methods for cloning nucleic acid molecules into vectors and for transforming host cells are well known in the art. For general descriptions of cloning, packaging, and expression systems and methods, see Giliman and Smith (1979) *Gene* 8:81-97; Roberts et al. (1987) *Nature* 328:731-734; Berger and Kimmel (1989) *Guide to Molecular Cloning Techniques, Methods in Enzymology*, Vol. 152 (Academic Press, Inc., San Diego, Calif.); Sambrook et al. (1989) *Molecular Cloning: A Laboratory Manual*, Vols. 1-3 (2d ed; Cold Spring Harbor Laboratory Press, Plainview, N.Y.); and Ausubel et al., eds. (1994) *Current Protocols in Molecular Biology, Current Protocols* (Greene Publishing Associates, Inc., and John Wiley & Sons, Inc., New York; 1994 Supplement.

Nucleic acid material, for example, plasmid preparations, from individual bacterial colonies comprising the PCR products from the second round of PCR is subjected to further analysis to identify putative novel pesticidal genes. In a particular embodiment, plasmid DNA from the individual colonies is analyzed by dot blot analysis using labeled oligonucleotide probes that are designed to detect all known pesticidal genes within the target group. The oligonucleotide probes are typically designed to be complementary to a fragment of the PCR products generated during the second round of PCR amplification. The probes are designed such that any nucleic acid containing a known pesticidal gene within the target group will be identified (i.e., "dot blot positives"). Any nucleic acids that are not detected by these probes using dot blot analysis (i.e., "dot blot negatives") contain putative novel pesticidal genes, or likely fragments thereof, and are further analyzed to assess novelty. The fragments of the putative novel pesticidal genes identified in accordance with the present methods are sequenced and subjected to sequence comparison with known pesticidal genes to assess novelty. Such sequence analyses are well known in the art. Novel nucleotide sequences are further analyzed to obtain putative pesticidal genes. In some embodiments, nucleic acid molecules comprising putative novel pesticidal genes are cloned into expression vectors and the polypeptides encoded by these genes are assayed for pesticidal activity using standard assays, such as those described herein below.

The above methods described for the identification of novel pesticidal genes may also be used to identify novel genes from other target groups of interest. When the methods of the invention are used to identify non-pesticidal genes, particularly non-Bt Cry toxin genes, the nucleic acid starting material may be obtained from a different organism of interest. The other method steps, however, namely the systematic primer design (described herein below), the first round of PCR, the second round of PCR, and the dot blot analysis are performed in essentially the same manner, regardless of the target group of genes of interest.

While not intending to be limited to any one mechanism, the oligonucleotide primers used in the first and second rounds of PCR amplification are designed to and likely permit the amplification of both known and novel 1 genes that contain signature sequences, as defined herein above. In contrast, the oligonucleotide probes used in the third step of the invention, typically dot blot analysis, are selected to specifically detect only known genes. Thus, organisms, such as microorganisms, particularly Bt strains, that comprise nucleic acid material that is amplified during the first and second rounds of PCR but is not detected during the dot blot analysis step may comprise a novel gene.

In particular aspects of the invention, designing at least one pair of oligonucleotide primers for use in the first round of PCR amplification described herein above comprises designing degenerate oligonucleotide primers via a multi-step process. In certain embodiments, an alignment of nucleotide sequences for a target group of genes is prepared. For example, a target group of pesticidal genes may comprise all known Cry genes that have pesticidal activity against insects from the order Coleopteran (i.e, Coleopteran-active genes). Genes within a target group share blocks of homology, referred to herein as signature sequences. The signature sequences serve as the starting point for oligonucleotide primer design, as described in detail below. Although a signature sequence is a block of nucleotides that is conserved within all members of the target group of genes, there may be some divergence in the signature sequence from gene to gene within the target group. As a result, it may not be possible to design a single set of oligonucleotide primers that will be specific for all genes in the target group. Therefore, a mixture of oligonucleotide primers may be used to cover all possible variations of the signature sequence appearing in the target group. Utilizing a mixture of oligonucleotide primers finds particular use when, because of sequence variations of the signature sequence within the target group of genes, it is difficult or impossible to develop one set of primers that is specific for a signature sequence within the entire target group. When possible, a single set of primers that is specific for as many genes within the target group as possible is designed and used. In certain aspects of the invention for the identification of novel Bt Cry toxin genes, the oligonucleotide primers used in the first round of PCR are designed to target signature sequences in "domain 1" of a target group of known Bt Cry genes, and those used in the second round of PCR are specific for sequences in "domain 2."

Designing degenerate oligonucleotide primers for use in the first and second rounds of PCR involves scanning the alignments of the nucleotide sequences of the target group of genes to identify several regions of homology that are appropriate starting points for the primer design described below. These regions of homology are referred to as "signature sequences." An initial primer length is selected, wherein the initial primer length is between about 15 base pairs (bp) and about 30 bp, for example, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, and 30 bp. A first round of screening for an oligonucleotide primer is then performed by viewing an initial window of contiguous nucleotides within one of the signature sequences. The initial window begins at the 5' end of the selected signature sequence and is equivalent in length to the initial primer length. The nucleotide sequence within the initial window is reviewed to determine if it possesses the following required sequence features. An appropriate nucleotide sequence for a primer for use in the first or second round of PCR:

1) does not have four or more contiguous identical nucleotide residues;

2) has no more than two guanine or cytosine residues within the last five residues of the 3' end of the nucleotide sequence;

3) has a melting temperature between about 50° C. and 65° C., more particularly about 54° C.±2° C.;

4) does not form hairpin or dimer structures;

5) is present in at least one of the nucleotide sequences from the target group of genes (i.e., the alignment described above); and, 6) is not conserved among nucleotide sequences from non-target group genes.

To increase the diversity of the oligonucleotide primers, one nucleotide residue is permitted to be n, wherein n is A, T, C, or G. A nucleotide sequence within the initial window is selected for use as an oligonucleotide primer if all of the above sequence features are present. If the nucleotide sequence within the initial window does not possess all of these sequence features, an adjacent window of contiguous nucleotides is selected by moving the initial window by one base pair toward the 3' end of the signature sequence. The nucleotide sequence within the adjacent window is reviewed as described above and selected for use as an oligonucleotide primer if all of the sequence features are present. Additional rounds of screening are performed as necessary to identify a nucleotide sequence satisfying the above requirements. An oligonucleotide within the signature sequence having the required features is selected and used as an oligonucleotide primer in the first or second round of PCR. Both forward and reverse primers are designed as described above. Furthermore, the forward and reverse primers used in the first round of PCR are designed such that they are complementary to nucleotide sequences within the genes in the target group that are about 50 bp to about 150 bp apart. The forward and reverse primers of the second round of PCR amplification are generally designed such that they are complementary to nucleotide sequences within the genes of the target group that are about 500 bp to about 800 bp apart.

As used herein above, a nucleotide sequence is "present" in at least one of the nucleotide sequences from target group of genes if the identical nucleotide sequence is found in the nucleotide sequence of at least one member of the target group, with the caveat that one nucleotide residue is permitted to be any nucleotide (i.e., n=A, T, C, or G). The term "non-target group of pesticidal genes" refers to all pesticidal genes within a particular family of pesticidal genes, excluding those pesticidal genes that have been selected as the target group. For example, if the target group comprises all Bt Cry genes that are Coleopteran-active, the corresponding non-target group of pesticidal genes comprises all Bt genes except those that are active against insects from the order Coleoptera. Similarly, a "non-target gene" or "non-target group of genes" refers to all genes within a particular family of pesticidal genes, excluding those genes that have been selected as the target group. A nucleotide sequence is "not conserved among nucleotide sequences from non-target group genes" if it differs from all nucleotide sequences within the non-target group by at least two nucleotide residues. In certain aspects of the invention, determining if a nucleotide sequence within a particular window of contiguous nucleotides is not conserved among non-target group genes comprises searching the full-length sequence of each gene from the non-target group of genes. In some embodiments, the full-length sequence of each gene from the non-target group of genes is exhaustively searched using the nucleotide sequence within the window as a string search term. That is, if a nucleotide sequence within a window appears anywhere in a non-target group gene or if a nucleotide sequence with less than 2 nucleotide residue differences appears anywhere in a non-target group gene, then that particular nucleotide sequence within the window will not be selected as an oligonucleotide primer.

As indicated above, the reverse primers used in the first round of PCR are typically used to generate the forward primers for the second round of PCR. The reverse primers for the second round of PCR are designed in accordance with the methods described above using a different signature sequence as the starting point for primer design, specifically one that is 3' to the signature sequence used to design the oligonucleotide primers for the first round of PCR. A schematic of exemplary primer design for the first and second rounds of PCR is presented in FIG. 1.

Because the signature sequences within the target group of genes will typically not be identical among all members, a mixture of oligonucleotide primers will generally be used in both the first and second rounds of PCR to account for these sequence variations. When mixtures of oligonucleotide primers are used in the PCR reactions of the invention, the primers will be further designed such that all primers have identical or nearly identical melting temperatures. In some embodiments, the melting temperature for oligonucleotide primers used in the first and second rounds of PCR will be about 54° C.±2° C.

"Pesticidal gene" refers to a nucleotide sequence that encodes a polypeptide that exhibits pesticidal activity. As used herein, the term "pesticidal activity" refers to the ability of a substance, such as a polypeptide, to inhibit the growth, feeding, or reproduction of an insect pest and/or to kill the insect pest. A "pesticidal polypeptide" or "insect toxin" is intended to mean a protein having pesticidal activity. Pesticidal activity can be measured by routine assays known in the art. Such assays include, but are not limited to, pest mortality, pest weight loss, pest repellency, pest attraction, and other behavioral and physical changes of a pest after feeding and exposure to the substance for an appropriate length of time. General procedures include addition of the experimental compound or organism to the diet source in an enclosed container. Assays for assessing pesticidal activity are well known in the art. See, e.g., U.S. Pat. Nos. 6,570,005 and 6,339,144; herein incorporated by reference in their entirety.

The preferred developmental stage for testing for pesticidal activity is larvae or immature forms of an insect of interest. The insects may be reared in total darkness at from about 20° C. to about 30° C. and from about 30% to about 70% relative humidity. Bioassays may be performed as described in Czapla and Lang (1990) *J. Econ. Entomol.* 83(6):2480-2485. Methods of rearing insect larvae and performing bioassays are well known to one of ordinary skill in the art.

In some embodiments of the invention, the target group of interest is pesticidal genes comprising Bt Cry toxin genes or a specific subset of Bt genes, such as, for example, Coleopteran-active Bt Cry genes. "Bt" or "*Bacillus thuringiensis*" gene is intended to mean the broader class of genes found in various strains of Bt that encode Bt toxins, which include such toxins as, for example, Cry (crystal) toxins (i.e., δ-endotoxins) and Cyt (cytotoxic) toxins. "Cry toxin" and "Cyt toxin" include pesticidal polypeptides that are homologous to known Cry or Cyt proteins, respectively. Cry genes include nucleotide sequences that encode any polypeptide classified as a Cry toxin, for example, Cry1, Cry2, Cry3, Cry7, Cry8 and Cry9. See, Crickmore et al. (1998) *Microbiol. Molec. Biol. Rev.* 62:807-813 and Crickmore et al. (2004) *Bacillus Thuringiensis Toxin Nomenclature* at lifesci.sussex.ac.uk/Home/Neil_Crickmore/B. thuringiensis, both of which are herein incorporated by reference in their entirety. The Bt toxins are a family of pesticidal proteins that are synthesized as protoxins and crystallize as parasporal inclusions. When ingested by an insect pest, the microcrystal structure is dissolved by the alkaline pH of the insect midgut, and the protoxin is cleaved by insect gut proteases to generate the active toxin. The activated Bt toxin binds to receptors in the gut epithelium of the insect, causing membrane lesions and associated swelling and lysis of the insect gut. Insect death results from starvation and septicemia. See, e.g., Li et al. (1991) *Nature* 353: 815-821.

The protoxin form of the Cry toxins contains a crystalline forming segment. A comparison of the amino acid sequences of active Cry toxins of different specificities further reveals five highly-conserved sequence blocks. Structurally, the Cry toxins comprise three distinct domains, which are, from the N- to C-terminus: a cluster of seven alpha-helices implicated in pore formation (referred to as "domain 1"), three antiparallel beta sheets implicated in cell binding (referred to as "domain 2"), and a beta sandwich (referred to as "domain 3"). The location and properties of these domains are known to those of skill in the art. See, for example, Li et al. (1991) supra and Morse et al. (2001) *Structure* 9:409-417.

The original Bt toxin nomenclature system classified the toxins on the basis of pesticidal activity profiles. This system has been replaced with a new nomenclature that is based solely on amino acid sequence identity. Under this system, the Cry and Cyt toxins have been grouped into classes or families based on amino acid sequence identity, and the name of the toxin provides information regarding its homology to other sequences. Thus, for example, the Cry2Aa, Cry2Ab, and Cry2Ac toxins, which are members of the Cry2 family, share approximately 80% amino acid sequence identity. Similarly, the Cry8 family toxins Cry8Aa and Cry8Ba share approximately 65% amino acid sequence identity. See Crickmore et al. (1998), supra.

The oligonucleotide primers specific for signature sequences within a target group of interest, such as a target group of pesticidal genes, used in both the first and second rounds of PCR and designed in accordance with the methods herein, are generally designed to have a thermal melting point ($T_m$) or temperature of between about 50° C. and 65° C. In particular embodiments, the oligonucleotide primers have a $T_m$ of between about 52° C. and 56° C., more particularly about 54° C. A number of formulas have been utilized for determining the $T_m$. Any formula for calculating $T_m$ can be used to practice the present methods. For example, a classic algorithm for $T_m$ determination based on nearest-neighbor thermodynamics is as follows:

$$T_m = EH°/(ES° + (R \times \ln(Ct)) - 273.15 + 16.6 \log [X]$$

where $EH°$ and $ES°$ are the enthalpy and entropy for helix formation, respectively; R is the molar gas constant (1.987 (cal)($K^{-1}$)($mol^{-1}$)); Ct is the total strand (primer) concentration; and X is the salt concentration. Rychlik et al. (1990) *Nucleic Acid Res.* 18(21):6409-6412. Moreover, in some embodiments, the $T_m$ of an oligonucleotide primer is calculated using the following formula:

$$T_m=(EH°/[ES°+(R\times\ln(Ct))]-273.15+16.6 \log([X]))\times 1.1144-14.964$$

where EH° (enthalpy)=$\Sigma\Delta H$; ES° (entropy)=$\Sigma\Delta S$+0.368×19×1.585; R (molar gas constant)=1.987; Ct (total primer concentration)=log (0.00000005/4)×1000; and X (salt concentration [K$^+$])=0.05.

A person skilled in the art will recognize that the oligonucleotide primers used to practice the methods of the invention are paired oligonucleotide primers such that there are two individual primers per pair (i.e., a forward primer and a reverse primer). One of the primers in each pair is complementary (i.e., capable of hybridizing) to a portion of the 5' strand of a signature sequence from the target group of genes (forward primer), while the other is complementary to a portion of the 3' strand of a signature sequence (reverse primer). The oligonucleotide primers are designed such that a suitable polymerase will copy the sequence of each strand 3' to each primer to produce amplified copies (i.e., the "PCR amplification product" or "PCR product"). The present methods utilize at least one pair of oligonucleotide primers for PCR amplification. In certain aspects of the invention, a mixture of oligonucleotide primer pairs comprising 2, 3, 4, 5, 10, 20, 30, 40, 50 or more primer pairs is used. Methods for designing oligonucleotide primers, including degenerate oligonucleotide primers, specific for particular nucleotide sequences of interest (e.g., signature sequences) are well known in the art.

The oligonucleotide primers of the present invention will be of a suitable length to permit amplification of novel genes, such as novel pesticidal genes. The individual primers of each pair will typically comprise between about 15 bp and about 30 bp, more particularly between about 20 bp and about 25 bp. The distance between the individual primers in a pair of oligonucleotide primers will also be sufficient to produce PCR products of a detectable length. Thus, in the first round of PCR, the forward and reverse primers are selected such that they are complementary to nucleotide sequences within the nucleotide sequences for members of the target group of genes that are typically between about 50 bp to about 150 bp apart, more particularly about 100 bp apart. In the second round of PCR, the forward and reverse primers will generally be complementary to nucleotide sequences within the target group that are between about 500 bp to about 800 bp apart, particularly about 600 bp to about 750 bp apart, more particularly about 600 to about 650 bp apart.

Nucleic acid material for use in the present methods may be obtained by any method from any organism of interest. Organisms of interest include, for example, microorganisms (more particularly Bt strains), plants, animals, fungi, bacteria, and insects. The nucleic acid material may comprise, for example, plasmid DNA prepared from an organism of interest, such as a Bt strain. In some embodiments, obtaining nucleic acid material comprises isolating DNA from an organism of interest, particularly a microorganism of interest. The nucleic acid material may comprise, for example, genomic DNA. In particular aspects of the invention, the nucleic acid material comprises a plasmid library generated from Bt strains. When multiple rounds of PCR amplification are performed, a new sample of nucleic acid material from the organism may be obtained and used for each round of PCR. Thus, for example, a new DNA plasmid preparation may be prepared from a Bt strain for use in each round of PCR.

Nucleic acid amplification by PCR is a fundamental molecular biology technique. Methods for performing PCR are well known in the art and can be performed on instrumentation that is commercially available. See, for example, Sambrook et al. (1989) *Molecular Cloning: A Laboratory Manual* (2d ed., Cold Spring Harbor Laboratory Press, Plainview, N.Y.); Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York), all of which are herein incorporated by reference. Briefly, PCR permits the rapid and efficient amplification of nucleic acid material (e.g., DNA from a gene of interest) comprising a target sequence of interest. The nucleic acid material to be amplified, the oligonucleotide primers, and a thermostable DNA polymerase (e.g., Taq polymerase) are mixed under conditions suitable for PCR amplification. PCR reaction mixes further comprise sufficient amounts of the four deoxynucleoside triphosphates and magnesium chloride. The individual reaction components for PCR are commercially available and are offered by a number of companies (e.g., Roche Diagnostics, Qiagen, Promega, Stratagene, etc.). Previously prepared reaction mixtures or "master mixes" to which only the nucleic acid material and the oligonucleotide primers have to be added are also available. PCR is performed for at least a time sufficient to allow for the production of copies of nucleic acid sequences between oligonucleotide primers in a detectable amount.

In particular embodiments, the methods of the invention comprise performing a first round of PCR, particularly real-time PCR, more particularly, quantitative real-time PCR. Real-time PCR permits the detection of PCR products at earlier stages of the amplification reaction. Specifically, in real-time PCR the quantitation of PCR products relies on the few cycles where the amount of nucleic acid material amplifies logarithmically until a plateau is reached. During the exponential phase, the amount of target nucleic acid material should be doubling every cycle, and there is no bias due to limiting reagents. Methods and instrumentation for performing real-time PCR are well known in the art. See, for example, Bustin (2000) *J. Molec. Endocrinol.* 25:169-193; Freeman et al. (1999) *Biotechniques* 112:124-125; Halford (1999) *Nat. Biotechnol.* 17:835; and Heid et al. (1996) *Genome Res.* 6(10):986-994, all of which are herein incorporated by reference in their entirety. In certain aspects of the invention, the first round of PCR amplification comprises performing real-time PCR.

As used herein, "detecting" PCR amplification products comprises any method for detecting the presence, absence, or quantity of nucleic acids amplified by the PCR steps of the present invention. Methods of detection may provide qualitative or quantitative information regarding the level of amplification. Such methods for detecting PCR amplification products are well known in the art and include, for example, ethidium-bromide stained agarose gel electrophoresis, Southern blotting/probe hybridization, and fluorescence assays.

Many different dyes and probes are available for monitoring PCR and detecting PCR products. For example, PCR products generated by real-time PCR amplification can be detected using a variety of fluorescent dyes and oligonucleotide probes covalently labeled with fluorescent molecules. Such fluorescent entities are capable of indicating the presence of PCR products and providing a signal related to the quantity of PCR products. Moreover, by using continuous fluorescence monitoring of the PCR products, the point at which the signal is detected above background (Ct; cycle threshold) and is in the exponential phase can be determined. The more abundant the template nucleic acid sequence the earlier the Ct is reached.

Double-stranded DNA-specific dyes can be used to detect PCR product formation in any PCR amplification without the need for synthesizing sequence-specific probes. Such dyes bind specifically to double-stranded DNA (dsDNA) and include but are not limited to SYBR® Green, SYBR Gold®, and ethidium bromide. "SYBR® Green" refers to any of the commercially available SYBR® Green fluorescent dyes, including SYBR® Green I and SYBR® Green II. With dsDNA dyes, product specificity can be increased by analysis of melting curves or by acquiring fluorescence at a high temperature where nonspecific products have melted. See Ririe et al. (1997) *Anal. Biochem.* 245:154-160; Morrison et al. (1998) *BioTechniques* 24:954-962.

Oligonucleotide probes can also be covalently labeled with fluorescent molecules and used to detect PCR products. Hairpin primers (Sunrise® primers), hairpin probes (Molecular Beacons®), and exonuclease probes (TaqMan® probes) are dual-labeled fluorescent oligonucleotides that can be monitored during PCR. These probes depend on fluorescence quenching of a fluorophore by a quencher on the same oligonucleotide. Fluorescence increases when hybridization or exonuclease hydrolysis occurs.

PCR products can also be detected using two oligonucleotides, each labeled with a fluorescent probe. Hybridization of these oligonucleotides to a target nucleic acid brings the two fluorescent probes close together to allow resonance energy transfer to occur. See, for example, Wittwer et al. (1997) *BioTechniques* 22:130-138. Acceptable fluorophore pairs for use as fluorescent resonance energy transfer pairs are well known to those skilled in the art and include, but are not limited to, fluorescein/rhodamine, phycoerythrin/Cy7, fluorescein/Cy5, fluorescein/Cy5.5, fluorescein/LC Red 640, and fluorescein/LC Red 705.

In certain aspects of the invention, a SYBR® Green fluorescent dye is used to detect PCR products, more particularly real-time PCR products generated during the first round of PCR. As described above, SYBR® Green is a fluorescent dye that binds the minor groove of dsDNA. When SYBR® Green dye binds to dsDNA, the intensity of the fluorescent emission increases. Thus, as more double-stranded PCR products are produced, the SYBR® Green fluorescent signal also increases. In other aspects of the invention, a 5' nuclease assay is used to monitor PCR, particularly real-time PCR, and to detect PCR amplification products. In the 5' nuclease assay, an oligonucleotide probe called a TaqMan® probe is added to the PCR reagent mix. The TaqMan® probe comprises a high-energy fluorescent reporter dye at the 5' end (e.g., FAM) and a low-energy quencher dye at the 3' end (e.g., TAMRA). When the probe is intact, the reporter dye's fluorescent emission is suppressed by the close proximity of the quencher. The TaqMan® probe is further designed to anneal to a specific sequence of template between the forward and reverse primers, and, therefore, the probe binds to the template nucleic acid material in the path of the polymerase. PCR amplification results in cleavage and release of the reporter dye from the quencher-containing probe by the nuclease activity of the polymerase. Thus, the fluorescence signal generated from the released reporter dye is proportional to the amount of the PCR product. Methods and instrumentation (e.g., ABI Prism 7700 Detector; Perkin Elmer/Applied Biosytems Division) for performing real-time PCR using SYBR® Green or TaqMan® probes are well known in the art. In particular embodiments, the PCR products from the first round of PCR amplification are detected using SYBR® Green.

As indicated above, PCR products generated during the second round of PCR are generally separated by agarose gel electrophoresis. Nucleic acid molecules of the expected length are isolated and subjected to dot blot analysis to eliminate known genes in the target group from further consideration.

"Dot blot analysis" or "dot blot hybridization" is a standard method in the field of molecular biology. In general, dot blot hybridization comprises immobilizing nucleic acid material on, for example, a nitrocellulose or nylon membrane. The immobilized nucleic acid material is exposed to a labeled oligonucleotide probe under conditions suitable for hybridization, and the presence or absence of bound probe is detected. Oligonucleotide probes of the invention may be labeled with a radioactive or non-radioactive label to facilitate detection of probe binding. Various radioactive and non-radioactive labels are available in the art. Such labels include, for example, digoxigenin (DIG), biotin, fluorescent molecules, and tritium ($^3$H). Methods for producing labeled oligonucleotide probes for use in dot blot analysis are well known in the art.

The oligonucleotide probes used for dot blot analysis in the methods of the invention are specific for all known genes (e.g., pesticidal genes) within the target group. The probes are designed to be complementary to fragments of the PCR products generated during the second round of PCR. A schematic of oligonucleotide probe design for the dot blot analysis step of the present invention is provided in FIG. 1. In particular embodiments, a mixture of oligonucleotide probes that are specific for all known genes in the target group are used. Designing a mixture of oligonucleotide probes, wherein each probe is specific for one gene within the target group, finds particular use when, because of sequence differences, it is difficult to develop a single probe that is specific for an entire target group. When possible, a single set of probes that is specific for as many genes (e.g., pesticidal genes) within the target group as possible is designed and used. Furthermore, when more than one oligonucleotide probe is used, the probes may be incubated with a single dot blot membrane as a mixture of probes or, alternatively, multiple membranes may be prepared and separately incubated with the individual probes. The dot blot oligonucleotide probes will typically be about 20 bp to about 40 bp in length, particularly about 25 bp to about 35 bp, more particularly about 30 bp to about 35 bp. Moreover, the oligonucleotide probes used for dot blot analysis will typically be designed to have a $T_m$ of at least about 70° C., particularly at least about 75° C., more particularly at least about 80° C. When a mixture of oligonucleotide probes is used, each probe will be designed to have approximately the same $T_m$.

One of skill in the art will appreciate that the methods or any of the steps therein, for identifying novel genes, including novel pesticidal genes, more particularly novel Bt Cry toxin genes, can be implemented in an automated, semi-automated, or manual fashion. The methods disclosed herein can be used in high-throughput screening assays.

The compositions of the invention include isolated polynucleotides, and variants and fragments thereof, comprising novel genes. Such novel genes are identified using the methods of the present invention. The amino acid sequences comprising polypeptides encoded by the nucleic acid molecules of the invention are further provided. Novel nucleic acid molecules and pesticidal polypeptides identified by the methods provided herein, find use, for example, in protecting plants from pest-related damage.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The use of the term "oligonucleotide" or "polynucleotide" is not intended to limit the present invention to polynucleotides comprising DNA. Those of ordinary skill in the art will recognize that oligonucleotides and polynucleotides, can comprise ribonucleotides and combinations of ribonucleotides and deoxyribonucleotides. Such deoxyribonucleotides and ribonucleotides include both naturally occurring molecules and synthetic analogues. The oligonucleotides and polynucleotides of the invention also encompass all forms of sequences including, but not limited to, single-stranded forms, double-stranded forms, and the like.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

As used herein, "full-length sequence" in reference to a specified polynucleotide or its encoded protein means having the entire nucleic acid sequence or the entire amino acid sequence of a native sequence. "Native sequence" is intended to mean an endogenous sequence, i.e., a non-engineered sequence found in an organism's genome. A full-length polynucleotide encodes the full-length form of the specified protein.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid molecule encoding a protein may comprise non-translated sequences (e.g., introns) within translated regions of the nucleic acid molecule or may lack such intervening non-translated sequences (e.g., as in cDNA).

Fragments and variants of the disclosed polynucleotides and proteins encoded thereby are also encompassed by the present invention. "Fragment" is intended to mean a portion of the polynucleotide or a portion of the amino acid sequence and hence protein encoded thereby. Fragments of a polynucleotide may encode protein fragments that retain the biological activity of the native protein and hence possess, for example, pesticidal activity. Alternatively, fragments of a polynucleotide that are useful as hybridization probes generally do not encode fragment proteins retaining biological activity. Thus, fragments of a polynucleotide may range from at least about 20 nucleotides, about 50 nucleotides, about 100 nucleotides, and up to the full-length polynucleotide encoding the proteins of the invention.

A fragment of a polynucleotide of the invention that encodes a biologically active portion of a protein will encode at least 15, 25, 30, 50, 100, 150, 200, or 250 contiguous amino acids, or up to the total number of amino acids present in a full-length protein of the invention, such as a pesticidal protein. Fragments of a polynucleotide that are useful as hybridization probes or PCR primers generally need not encode a biologically active portion of the protein.

Thus, a fragment of a polynucleotide may encode a biologically active portion of a protein, or it may be a fragment that can be used as a hybridization probe or PCR primer using methods disclosed below. A biologically active portion of a protein can be prepared by isolating a portion of one of the polynucleotides of the invention, expressing the encoded portion of the protein (e.g., by recombinant expression in vitro), and assessing the biological activity of the encoded portion of the protein. Polynucleotides that are fragments of a nucleotide sequence identified by the methods herein comprise at least 16, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length polynucleotide disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a biologically active protein of the invention (e.g., a pesticidal protein). Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to a polypeptide of the invention are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, for example, pesticidal activity as described herein. Such variants may result from, for example, genetic polymorphism or from human manipulation. Biologically active variants of a native protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of pesticidal or other proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the polynucleotides of the invention include both the naturally occurring sequences as well as mutant forms. Likewise, the proteins of the invention encompass both naturally occurring proteins as well as variations and modified forms thereof. Such variants will continue to possess the desired biological activity, for example, pesticidal activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. For example, the activity of variants of novel pesticidal proteins can be evaluated by assaying for pesticidal activity. See, for example, U.S. Pat. Nos. 6,570,005 and 6,339,144, herein incorporated by reference.

Variant polynucleotides and proteins also encompass sequences and proteins derived from a mutagenic and recombinogenic procedure such as DNA shuffling. With such a procedure, one or more different protein coding sequences can be manipulated to create a new polypeptide possessing the desired properties, such as pesticidal activity. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the gene of the invention (e.g., a novel Bt Cry toxin gene) and other known related genes to obtain a new gene coding for a protein with an improved property of interest, such as increased pesticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other microorganisms. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for a polypeptide with a biological activity of interest and that hybridize under stringent conditions to a sequence disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the pesticidal polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

While the present invention provides more efficient methods for identifying novel genes that share homologous regions (i.e., signature sequences) with any target group of known genes of interest, particularly novel pesticidal genes, more particularly novel Bt Cry toxin genes, one of skill in the art will recognize that standard methods known in the art can also be used to identify sequences that are homologous to the polynucleotides disclosed herein. For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique among the polynucleotide sequences and are optimally at least about 10 nucleotides in length, and most optimally at least about 20 nucleotides in length. Such probes may be used to amplify corresponding polynucleotides (e.g., pesticidal polynucleotides) from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. "Stringent conditions" or "stringent hybridization conditions" is intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence," (b) "comparison window," (c) "sequence identity," and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The methods of the present invention may be used to identify novel genes that share regions of homology with any target group of known genes. In one embodiment, the instant methods are used to identify novel pesticidal genes that are effective against a variety of pests. For purposes of the present invention, pests include, but are not limited to, insects, fungi, bacteria, nematodes, acarids, protozoan pathogens, animal-parasitic liver flukes, and the like. Pests of particular interest are insect pests, particularly insect pests that cause significant damage to agricultural plants. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

Although the instant methods may be used to identify novel genes that are homologous to any target group of known genes, the present invention may, for example, be used to identify novel pesticidal genes that encode polypeptides that protect any plant species from pest-related damage, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The article "a" and "an" are used herein to refer to one or more than one (i.e., to at least one) of the grammatical object of the article. By way of example, "an element" means one or more element.

The following examples are provided by way of illustration, not by way of limitation.

EXPERIMENTAL

Example 1

Identification of Novel Pesticidal Genes

Isolation of Bt Plasmid DNA

Glycerol stocks of various Bt strains were streaked onto LB agar plates. The following day, a single colony from each strain was inoculated into 2 mL of TB media per well of a 48-well plate. The plates were incubated overnight at 28° C. and 250 rpm. The cells were harvested by centrifugation at 6,000×g for 10 minutes at room temperature. The cell pellets were resuspended by vortexing in P1 suspension buffer (Qiagen). Cells were lysed and neutralized with P2 and P3 buffers, respectively, and the lysates were transferred to TurboFilters (Qiagen) with vacuum applied. The filtrates were bound to QIAprep plates and washed with PB and PE buffers (Qiagen). The plasmid preparations were eluted with EB buffer and collected in 96-well plates.

Degenerate Oligonucleotide Primer Design for the First Round of PCR

In order to identify novel Bt genes, both those that are homologous to known Cry genes as well as pesticidal genes that represent novel Cry gene families, oligonucleotide primers were designed to regions of high homology within a target group of known Bt genes of interest. In the present example, the target group comprised known Cry genes that have pesticidal activity against insect from the orders Leptidoptera and Coleoptera but not those Cry genes that are Dipteran-active. Specifically, the nucleotide sequences for all the known Bt Cry genes from the target group were collected from the public database, and an alignment of these sequences was generated. Several DNA regions along the nucleotide sequences that were appropriate for the strict primer design requirements were located in all the chosen Bt genes. Those regions were coined "signature sequence" for insecticidal Bt genes as a few DNA sequences (17 to 24 continuous nucleotides) were present in all known insecticidal Bt genes.

An initial primer length was selected to give a $T_m$ of 54° C., and a window of contiguous nucleotides beginning at the 5' end of the selected signature sequence was viewed. Specifically, the nucleotide sequence within the window was reviewed to determine if the following sequence features were present:

1) does not have four or more contiguous identical nucleotide residues;

2) has no more than two guanine or cytosine residues within the last five residues of the 3' end of the nucleotide sequence;

3) has a melting temperature $T_m$ fixed at 54° C.±2° C.

4) does not form hairpin or dimer structures;

5) is present in at least one of the nucleotide sequences from the target group of pesticidal genes (i.e., the alignment); and, 6) is not conserved among nucleotide sequences from non-target group pesticidal genes.

To increase diversity within the primer, one base pair was allowed to be n, wherein n was selected from the group consisting of adenine, thymine, cytosine, and guanine.

If all sequence features were present, the nucleotide sequence within the window of nucleotides was selected for use as an oligonucleotide primer for the first round of PCR. If the nucleotide sequence within the window did not possess the required sequence features, then an adjacent window of contiguous nucleotides was selected by moving 1 bp closer to the 3' end of the signature, and the process was repeated. Both a forward and a reverse oligonucleotide primer were designed in accordance with the present methods. Furthermore, the forward and reverse primers were designed such that they were complementary to nucleotide sequences in the pesticidal genes of interest that are about 50 bp to about 150 bp apart. A schematic of the general primer design methodology for the first round of PCR is provided in FIG. 1.

First Round of PCR Amplification: SYBR® Green Step

A first round of PCR amplification of a first sample of nucleic acid material isolated from a Bt strain was performed using the oligonucleotide primers designed as described above. Specifically, the Bt plasmid preparations in 96-well plates were amplified by PCR under the following reaction conditions:

Template DNA amount: 100 ng

Primer amount: 7.5 nmole (5 μM×1.5 μL)

Volume of reaction mixture: 25 μL

AmpliTag® Gold DNA polymerase activation: 95° C. for 10 min

PCR cycle (40 cycles): 95° C. for 15 sec; 60° C. 1 min

PCR products from the first round of amplification were detected using a SYBR® Green fluorescent dye and the 7700 ABI Prism Sequence Detection System in accordance with methods known in the art. A plasmid preparation from DP strain 1218-1 that comprises the Cry8Bb1 gene was used as a positive control. See pending U.S. patent application Ser. No. 10/032,717, entitled "Genes Encoding Novel Proteins with Pesticidal Activity Against Coleopterans," filed Oct. 23, 2001, which is herein incorporated by reference in its entirety. Using the PCR conditions described above, the 1218-1 plasmid preparation produced a standard curve for PCR amplification in the 7700 ABI Prism Sequence Detection System, and a Ct value of approximately 13 was obtained for the positive control. A negative control comprising only the PCR reaction mixture without template DNA was tested and generated a Ct value of approximately 35. Bt plasmid preparations that produced a Ct value of below 16 were selected for further analysis and were designated a SYBR® Green positives.

Second Round of PCR

All reverse primers from the SYBR® Green primer set (i.e., the reverse oligonucleotide primers used the first round of PCR) were used to generate the forward primers for the second round of PCR (i.e., the reverse template of the first round primers). These primers functioned as the bridge between the SYBR® Green step (i.e., first round of PCR) and the second round of PCR. The reverse primers for use in the second round of PCR were designed essentially as described above for the first round oligonucleotide primers. The PCR primer $T_m$ was kept at 54° C.±2° C. and designed to generate a fragment of about 650 bp to about 700 bp. A schematic of the general primer design methodology for the second round of PCR is provided in FIG. 1.

Plasmid DNA was isolated from Bt strains identified as SYBR® Green positives in the first round of PCR and then subjected to a second round of PCR. The PCR conditions for the second round were as follows, using the Qiagen Multiplex PCR kit and the Bt plasmid preparations described above:

DNA 0.5 μg

Program:

95° C. 15 min

94° C. 30 sec

54° C. 1.5 min

72° C. 1.5 min

35× from step 2 to step 4

72° C. 10 min

4° C. indefinitely

The PCR reactions from the second round were analyzed with 1.0% agarose gel electrophoresis, and the expected fragments of 650 bp to 700 bp were then cloned into bacterial cloning vectors using a blunt Vector kit (Invitrogen). After ligation, the products were transformed into Top 10 *E. coli* competent cells (Invitrogen). Plasmid DNA from individual bacterial colonies were prepared and analyzed by dot blot analysis, as described below.

Dot Blot Analysis

In order to eliminate known Bt genes from analysis and to identify novel pesticidal genes comprising the signature sequences used in the first and second rounds of PCR, dot blot analysis was performed. Specifically, the plasmid DNA from isolated from the individual bacterial colonies was blotted onto nylon positively charged membrane (Roche). Probe specific for all pesticidal genes within the target group were designed to be within the DNA expected sequence fragment generated during the second round of PCR. A schematic of the general probe design methodology for the dot blot step is provided in FIG. 1. All probes were designed to have a $T_m$ of about 74° C.±2° C. In all three steps (i.e., the first round of PCR, the second round of PCR, and dot blot analysis), the $T_m$ of the oligonucleotide primers/probes was fixed so that a mixture of primers/probes could be used at each step. The oligonucleotide probes were labeled using the DIG oligonucleotide 3' end labeling Kit (Roche) and used to screen the dot blot for known Bt genes. Every probe was tested individually and in a mixture of probes to ensure specificity and validity of each probe.

All plasmid preparations characterized as positive for known Bt genes by dot blot analysis were eliminated from further analysis. Plasmid preparations that were negative when analyzed by dot blot were subjected to further sequence analysis, as described below, to assess novelty.

Sequence Analysis

Nucleic acids generated during the second round of PCR (i.e., 650 bp to 700 bp fragments) and characterized as "negative" by dot blot analysis were sequenced. Sequence results of these nucleic acids were compared against nucleotide sequences available in public databases using BLAST. If the sequence analysis indicated a potentially novel Bt gene, the nucleotide sequence for the full-length gene was obtained using the GenomeWalker Universal Kit (Becton Dickinson Bioscience). The nucleotide sequence of the full-length putative novel pesticidal gene was further analyzed as described above to confirm novelty. Novel pesticidal genes, such as those set forth in SEQ ID NOs:1, 3, and 5 (and the polypeptides encoded thereby set forth in SEQ ID NOs:2, 4, and 6, respectively) were identified by the present methods. Novel pesticidal genes were tested for pesticidal activity, as described below.

Bioassays

Novel pesticidal genes were cloned into expression vectors and assayed for pesticidal activity against maize insect pests. Such methods are generally known in the art. Methods for assaying for pesticidal activity against Coleopterans are known in the art and described in, for example, U.S. Patent Application Publication No. 2002/0151709. Assays for pesticidal activity against Lepidopterans are disclosed in, for example, U.S. Patent Application Publication No. 2005/0138684.

Results

The results of the bioassays are presented in Table 1 and 2.

TABLE 1

Novel pesticidal genes with Lepidopteran activity

| | GS001 (SEQ ID NO: 3) | GS021 (SEQ ID NO: 1) |
|---|---|---|
| *Ostrinia nubilalis* (ECB) | + | + |
| *Helicoverpa zea* (CEW) | + | + |
| *Agrotis ipsilon* (BCW) | + | + |
| *Spodoptera frugiperda* (FAW) | − | − |

TABLE 2

Novel pesticidal gene with Coleopteran activity

| | GS028 (SEQ ID NO: 5) |
|---|---|
| *Diabrotica virgifera* LeConte (WCRW) | + |
| *Diabrotica undecimpunctata* (SCRW) | − |
| *Leptinotarsa decemlineata* (CPB) | − |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for identifying novel pesticidal genes, the method comprising:
   a) designing at least one pair of oligonucleotide primers for use in a first round of PCR that is specific for a target group of pesticidal genes, the pair of primers comprising a forward primer and a reverse primer, wherein each primer targets a signature sequence present in the nucleotide sequences of the target group, wherein said designing comprises:
      i) preparing an alignment of all nucleotide sequences from the target group;
      ii) identifying signature sequences within the nucleotide sequences of the target group of pesticidal genes, wherein a signature sequence comprises a region of homology between all members of the target group;
      iii) selecting an initial primer length, wherein the initial primer length is between 15 bp and 30 bp;
      iv) performing a first round of screening for an oligonucleotide primer sequence, the screening comprising viewing an initial window of contiguous nucleotides of a signature sequence within the nucleotide sequences of the target group, wherein the initial window is initiated at the 5' end of the nucleotide sequence of the signature sequence;

v) determining if the nucleotide sequence within the initial window has the sequence features of (1)-(6) below
   (1) does not have four or more contiguous identical nucleotide residues;
   (2) has no more than two guanine or cytosine residues within the last five residues of the 3' end of the nucleotide sequence;
   (3) has a $T_m$ between 50° C. and 65° C.;
   (4) does not form hairpin or dimer structures;
   (5) is present in at least one of the nucleotide sequences from the target group of pesticidal genes; and
   (6) is not conserved among nucleotide sequences from non-target group pesticidal genes;
   wherein one nucleotide residue within the initial window of contiguous nucleotide sequences is permitted to be n, wherein n is any nucleotide selected from the group consisting of adenine, thymine, guanine, and cytosine;
vi) selecting the nucleotide sequence within the initial window for use as an oligonucleotide primer if all of the sequence features of step (v) are present;
vii) selecting an adjacent window of contiguous nucleotides by moving the first window toward the 3' end of the signature sequence within the nucleotide sequences of the target group by one base pair if the nucleotide sequence within the initial window does not have all of the sequence features of step v), wherein the adjacent window is equivalent in length to the initial primer length;
viii) repeating steps v)-vii) with the adjacent window until a nucleotide sequence with all of the sequence features is identified or until the entire signature sequence for the target group is screened; and
ix) selecting a second signature sequence within the nucleotide sequences of the target group of pesticidal genes and performing additional rounds of screening comprising repeating steps iii) through viii) using the second signature sequence if no nucleotide sequence with all of the features is identified by screening the first signature sequence;
b) obtaining a first sample of nucleic acid material from a microorganism of interest;
c) mixing the first sample of nucleic acid material with the at least one pair of oligonucleotide primers for use in the first round of PCR and a thermostable DNA polymerase under conditions that are suitable for amplification by PCR;
d) performing a first round of PCR and detecting PCR amplification products, thereby determining if PCR products are produced in the first round of PCR;
e) obtaining a second sample of nucleic acid material from the microorganism if PCR products are detected in the first round of PCR;
f) designing at least one pair of oligonucleotide primers for use in a second round of PCR that is specific for the target group of pesticidal genes, the pair of primers comprising a forward primer and a reverse primer, wherein each primer targets a signature sequence present in the nucleotide sequences of the target group, and wherein said at least one pair of oligonucleotide primers for use in the second round of PCR does not comprise the nucleotide sequences of said at least one pair of oligonucleotide primers of (a);
g) mixing the second sample of nucleic acid material with the at least one pair of oligonucleotide primers for use in the second round of PCR and a thermostable DNA polymerase under conditions that are suitable for amplification by PCR and performing a second round of PCR;
h) separating any PCR amplification products produced in the second round of PCR using agarose gel electrophoresis and isolating nucleic acid fragments for further analysis, wherein the nucleic acid fragments may comprise a putative novel pesticidal gene fragment;
i) cloning each nucleic acid fragment into a cloning vector;
j) transforming host cells with the cloning vectors, wherein the cloning vectors comprise the nucleic acid fragments isolated in step (h);
k) preparing nucleic acid samples from individual host colonies comprising a cloning vector;
l) subjecting the nucleic acid samples from the individual host colonies to dot blot analysis using labeled probes that are specific for all known pesticidal genes from the target group, wherein a nucleic acid fragment isolated in step (h) that is not detected during the dot blot analysis step comprises a putative novel pesticidal gene fragment; and
m) analyzing the putative novel pesticidal gene fragment.

2. The method of claim 1, wherein the microorganism of interest comprises a *Bacillus thuringiensis* strain.

3. The method of claim 2, wherein obtaining a first and second sample of nucleic acid material from the microorganism of interest comprises preparing plasmid DNA from the *Bacillus thuringiensis* strain.

4. The method of claim 1, wherein obtaining nucleic acid material from the microorganism of interest comprises isolating DNA.

5. The method of claim 1, wherein the target group of pesticidal genes comprises *Bacillus thuringiensis* Cry genes.

6. The method of claim 5, wherein the target group comprises *Bacillus thuringiensis* Cry genes that have pesticidal activity against insects from the order Coleoptera.

7. The method of claim 1, wherein the first round of PCR comprises performing quantitative real-time PCR.

8. The method of claim 7, wherein the first round of PCR is performed in the presence of a fluorescent entity, the fluorescent entity being capable of indicating the presence of PCR products and providing a signal related to the quantity of PCR products.

9. The method of claim 8, wherein the fluorescent entity is a dye.

10. The method of claim 1, wherein the labeled probes that are specific for all known pesticidal genes from the target group used for dot blot analysis are designed to be specific for a region present in the nucleic acid fragments generated during the second round of PCR.

11. The method of claim 1, wherein the labeled probes used for dot blot analysis have a thermal melting temperature ($T_m$) of 70° C. to 85° C.

12. The method of claim 11, wherein the $T_m$ is 80° C.

13. The method of claim 5, wherein the at least one pair of oligonucleotide primers used in the first round of PCR is designed to be specific for a nucleotide sequence present in domain 1 of the *Bacillus thuringiensis* Cry genes.

14. The method of claim 5, wherein the at least one pair of oligonucleotide primers used in the second round of PCR is designed to be specific for a nucleotide sequence present in domain 2 of the *Bacillus thuringiensis* Cry genes.

15. The method of claim 1, wherein the $T_m$ for the at least one pair of oligonucleotide primers used in the first and second rounds of PCR is 50° C. to about 65° C.

16. The method of claim 15, wherein the $T_m$ is 52° C. to 56° C.

17. The method of claim 1, wherein analyzing the putative novel pesticidal gene fragment comprises nucleotide sequence analysis.

18. The method of claim 17, wherein the nucleotide sequence analysis comprises sequencing the nucleic acid comprising a putative novel pesticidal gene fragment and comparing the nucleotide sequence of the putative novel pesticidal gene fragment with all known pesticidal genes, thereby determining if the fragment is novel.

19. The method of claim 18 further comprising sequencing the full-length putative novel pesticidal gene if the fragment is determined to be novel.

20. The method of claim 19 further comprising cloning the novel pesticidal gene into a cloning vector and assessing the pesticidal activity of the polypeptide encoded by the novel pesticidal gene.

21. The method of claim 20, wherein assessing the pesticidal activity comprises performing a bioassay.

22. The method of claim 1, wherein at least one forward primer for the second round of PCR is the complement of a reverse primer of the first round of PCR.

23. The method of claim 1, wherein the forward and reverse oligonucleotide primers used in the first round of PCR are complementary to nucleotide sequences within the target group of pesticidal genes that are between 50 base pairs (bp) to 150 bp apart.

24. The method of claim 1, wherein the oligonucleotide primers used in the second round of PCR are designed to generate fragments of 600 bp to 750 bp in length.

25. The method of claim 24, wherein the oligonucleotide primers used in the second round of PCR are designed to generate fragments of 650 bp to 700 bp in length.

26. The method of claim 1, wherein the $T_m$ is 52° C. to 56° C.

27. The method of claim 1, wherein said at least one pair of primers designed for use in the first round of PCR are a mixture of degenerate oligonucleotide primer pairs.

28. The method of claim 27, wherein the mixture of degenerate oligonucleotide primer pairs designed in accordance with claim 30 is used in the first round of PCR.

29. The method of claim 1, wherein designing at least one pair of oligonucleotide primers for use in the second round of PCR that is specific for the target group of pesticidal genes comprises:
    a) using a reverse oligonucleotide primer from the first round of PCR to generate a forward oligonucleotide primer in the second round of PCR, wherein at least one forward primer for the second round of PCR is generated by making a primer comprising the complement of a reverse primer of the first round of PCR;
    b) preparing an alignment of all nucleotide sequences from the target group of pesticidal genes to design a reverse oligonucleotide primer for use in the second round of PCR;
    c) identifying signature sequences within the nucleotide sequences of the target group, wherein a signature sequence comprises a region of homology between all members of the target group, and wherein the signature sequence used to design the reverse primer for the second round of PCR is located 3' to the signature sequence used to design the reverse oligonucleotide primer used in the first round of PCR;
    d) performing steps i) through ix) of claim 1 until a nucleotide sequence with all of the sequence features recited in 1)-6) of claim 1 is identified and selecting the nucleotide sequence for use as a reverse primer in the second round of PCR.

30. The method of claim 29, wherein the $T_m$ is 52° C. to 56° C.

31. The method of claim 29, wherein said at least one pair of oligonucleotide primers designed for use in the second round of PCR are a mixture of degenerate oligonucleotide primer pairs.

32. The method of claim 31, wherein the mixture of degenerate oligonucleotide primer pairs designed in accordance with claim 31 are used in the second round of PCR.

33. The method of claim 1, wherein a mixture of degenerate oligonucleotide primer pairs designed in accordance with claim 27 is used in the first round of PCR, and wherein a mixture of degenerate oligonucleotide primer pairs designed in accordance with claim 34 is used in the second round of PCR.

34. A method for identifying novel genes that share homology with a target group of known pesticidal genes, the method comprising:
    a) designing at least one pair of oligonucleotide primers for use in a first round of PCR that is specific for the target group of pesticidal genes, the pair of primers comprising a forward primer and a reverse primer, wherein each primer targets a signature sequence present in the nucleotide sequences of the target group, wherein said designing comprises
        i) preparing an alignment of all nucleotide sequences from the target group;
        ii) identifying signature sequences within the nucleotide sequences of the target group of pesticidal genes, wherein a signature sequence comprises a region of homology between all members of the target group;
        iii) selecting an initial primer length, wherein the initial primer length is between 15 bp and 30 bp;
        iv) performing a first round of screening for an oligonucleotide primer sequence, the screening comprising viewing an initial window of contiguous nucleotides of a signature sequence within the nucleotide sequences of the target group, wherein the initial window is initiated at the 5' end of the nucleotide sequence of the signature sequence;
        v) determining if the nucleotide sequence within the initial window has the sequence features of (1)-(6) below
            (1) does not have four or more contiguous identical nucleotide residues;
            (2) has no more than two guanine or cytosine residues within the last five residues of the 3' end of the nucleotide sequence;
            (3) has a $T_m$ between 50° C. and 65° C.;
            (4) does not form hairpin or dimer structures;
            (5) is present in at least one of the nucleotide sequences from the target group of pesticidal genes; and
            (6) is not conserved among nucleotide sequences from non-target group pesticidal genes;
        wherein one nucleotide residue within the initial window of contiguous nucleotide sequences is permitted to be n, wherein n is any nucleotide selected from the group consisting of adenine, thymine, guanine, and cytosine;
        vi) selecting the nucleotide sequence within the initial window for use as an oligonucleotide primer if all of the sequence features of step (v) are present;
        vii) selecting an adjacent window of contiguous nucleotides by moving the first window toward the 3' end of the signature sequence within the nucleotide sequences of the target group by one base pair if the nucleotide sequence within the initial window does not have all of the sequence features of step v), wherein the adjacent window is equivalent in length to the initial primer length;

viii) repeating steps v)-vii) with the adjacent window until a nucleotide sequence with all of the sequence features is identified or until the entire signature sequence for the target group is screened; and ix) selecting a second signature sequence within the nucleotide sequences of the target group of pesticidal genes and performing additional rounds of screening comprising repeating steps iii) through viii) using the second signature sequence if no nucleotide sequence with all of the features is identified by screening the first signature sequence;

b) obtaining a first sample of nucleic acid material from an organism of interest;

c) mixing the first sample of nucleic acid material with the at least one pair of oligonucleotide primers for use in the first round of PCR and a thermostable DNA polymerase under conditions that are suitable for amplification by PCR;

d) performing a first round of PCR and detecting PCR amplification products, thereby determining if PCR products are produced in the first round of PCR;

e) obtaining a second sample of nucleic acid material from the organism if PCR products are detected in the first round of PCR;

f) designing at least one pair of oligonucleotide primers for use in a second round of PCR that is specific for the target group of pesticidal genes, the pair of primers comprising a forward primer and a reverse primer, wherein each primer targets a signature sequence present in the nucleotide sequences of the target group, and wherein said at least one pair of oligonucleotide primers for use in the second round of PCR does not comprise the nucleotide sequences of said at least one pair of oligonucleotide primers of (a);

g) mixing the second sample of nucleic acid material with the at least one pair of oligonucleotide primers for use in the second round of PCR and a thermostable DNA polymerase under conditions that are suitable for amplification by PCR and performing a second round of PCR;

h) separating any PCR amplification products produced in the second round of PCR using agarose gel electrophoresis and isolating nucleic acid fragments for further analysis, wherein the nucleic acid fragments may comprise a putative novel gene fragment that shares homology with the genes of the target group of pesticidal genes;

i) cloning each nucleic acid fragment into a cloning vector;

j) transforming host cells with the cloning vectors, wherein the cloning vectors comprise the nucleic acid fragments isolated in step (h);

k) preparing nucleic acid samples from individual host colonies comprising a cloning vector;

l) subjecting the nucleic acid samples from the individual host colonies to dot blot analysis using labeled probes that are specific for all known genes from the target group, wherein a nucleic acid fragment isolated in step (h) that is not detected during the dot blot analysis step comprises a putative novel gene fragment that shares homology with the genes of the target group; and m) analyzing the putative novel gene fragment.

35. A method for identifying novel pesticidal genes, the method comprising:

a) designing at least one pair of oligonucleotide primers for use in a first round of PCR that is specific for a target group of pesticidal genes, the pair of primers comprising a forward primer and a reverse primer, wherein each primer targets a signature sequence present in the nucleotide sequences of the target group;

b) obtaining a first sample of nucleic acid material from a microorganism of interest;

c) mixing the first sample of nucleic acid material with the at least one pair of oligonucleotide primers for use in the first round of PCR and a thermostable DNA polymerase under conditions that are suitable for amplification by PCR;

d) performing a first round of PCR and detecting PCR amplification products, thereby determining if PCR products are produced in the first round of PCR, wherein the first round of PCR comprises performing quantitative real-time PCR;

e) obtaining a second sample of nucleic acid material from the microorganism if PCR products are detected in the first round of PCR;

f) designing at least one pair of oligonucleotide primers for use in a second round of PCR that is specific for the target group of pesticidal genes, the pair of primers comprising a forward primer and a reverse primer, wherein each primer targets a signature sequence present in the nucleotide sequences of the target group, and wherein said at least one pair of oligonucleotide primers for use in the second round of PCR does not comprise the nucleotide sequences of said at least one pair of oligonucleotide primers of (a);

g) mixing the second sample of nucleic acid material with the at least one pair of oligonucleotide primers for use in the second round of PCR and a thermostable DNA polymerase under conditions that are suitable for amplification by PCR and performing a second round of PCR;

h) separating any PCR amplification products produced in the second round of PCR using agarose gel electrophoresis and isolating nucleic acid fragments for further analysis, wherein the nucleic acid fragments may comprise a putative novel gene fragment that shares homology with the pesticidal genes of the target group;

i) cloning each nucleic acid fragment into a cloning vector;

j) transforming host cells with the cloning vectors, wherein the cloning vectors comprise the nucleic acid fragments isolated in step (h);

k) preparing nucleic acid samples from individual host colonies comprising a cloning vector;

l) subjecting the nucleic acid samples from the individual host colonies to dot blot analysis using labeled probes that are specific for all known pesticidal genes from the target group, wherein a nucleic acid fragment isolated in step (h) that is not detected during the dot blot analysis step comprises a putative novel pesticidal gene fragment; and m) analyzing the putative novel pesticidal gene fragment.

36. A method for identifying novel pesticidal genes, the method comprising:

a) designing at least one pair of oligonucleotide primers for use in a first round of PCR that is specific for a target group of pesticidal genes, the pair of primers comprising a forward primer and a reverse primer, wherein each primer targets a signature sequence present in the nucleotide sequences of the target group;

b) obtaining a first sample of nucleic acid material from a microorganism of interest;

c) mixing the first sample of nucleic acid material with the at least one pair of oligonucleotide primers for use in the first round of PCR and a thermostable DNA polymerase under conditions that are suitable for amplification by PCR;

d) performing a first round of PCR and detecting PCR amplification products, thereby determining if PCR products are produced in the first round of PCR;

e) obtaining a second sample of nucleic acid material from the microorganism if PCR products are detected in the first round of PCR;

f) designing at least one pair of oligonucleotide primers for use in a second round of PCR that is specific for the target group of pesticidal genes, the pair of primers comprising a forward primer and a reverse primer, wherein each primer targets a signature sequence present in the nucleotide sequences of the target group, and wherein said at least one pair of oligonucleotide primers for use in the second round of PCR does not comprise the nucleotide sequences of said at least one pair of oligonucleotide primers of (a);

g) mixing the second sample of nucleic acid material with the at least one pair of oligonucleotide primers for use in the second round of PCR and a thermostable DNA polymerase under conditions that are suitable for amplification by PCR and performing a second round of PCR;

h) separating any PCR amplification products produced in the second round of PCR using agarose gel electrophoresis and isolating nucleic acid fragments for further analysis, wherein the nucleic acid fragments may comprise a putative novel pesticidal gene fragment;

i) cloning each nucleic acid fragment into a cloning vector;

j) transforming host cells with the cloning vectors, wherein the cloning vectors comprise the nucleic acid fragments isolated in step (h);

k) preparing nucleic acid samples from individual host colonies comprising a cloning vector;

l) subjecting the nucleic acid samples from the individual host colonies to dot blot analysis using labeled probes that are specific for all known pesticidal genes from the target group, wherein a nucleic acid fragment isolated in step (h) that is not detected during the dot blot analysis step comprises a putative novel pesticidal gene fragment; and m) analyzing the putative novel pesticidal gene fragment;

wherein the $T_m$ for the at least one pair of oligonucleotide primers used in the first and second rounds of PCR is 50° C. to 65° C.

* * * * *